(12) United States Patent
Saitoh et al.

(10) Patent No.: US 8,273,902 B2
(45) Date of Patent: Sep. 25, 2012

(54) PROCESS FOR PRODUCTION OF 1-(3-(2-(1-BENZOTHIOPHEN-5-YL)-ETHOXY)PROPYL)AZETIDIN-3-OL OR SALTS THEREOF

(75) Inventors: Akihito Saitoh, Toyama (JP); Yoshiaki Suzuki, Toyama (JP); Kenji Yonezawa, Toyama (JP); Mitsuhide Kawamura, Toyama (JP); Takahiko Kusanagi, Toyama (JP); Takashi Nakai, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/985,616

(22) Filed: Jan. 6, 2011

(65) Prior Publication Data

US 2011/0098484 A1 Apr. 28, 2011

Related U.S. Application Data

(62) Division of application No. 11/909,809, filed as application No. PCT/JP2006/306127 on Mar. 27, 2006, now Pat. No. 7,951,963.

(30) Foreign Application Priority Data

| Mar. 28, 2005 | (JP) | 2005-090831 |
| Jun. 15, 2005 | (JP) | 2005-174738 |
| Jul. 15, 2005 | (JP) | 2005-206808 |
| Aug. 9, 2005 | (JP) | 2005-230666 |

(51) Int. Cl.
C07D 205/00 (2006.01)
C07D 333/72 (2006.01)

(52) U.S. Cl. .................. 548/953; 549/58
(58) Field of Classification Search .......... 548/953; 549/58
See application file for complete search history.

(56) References Cited

U.S. PATENT DOCUMENTS

| 4,668,697 A | 5/1987 | Shepard et al. |
| 2009/0069576 A1 | 3/2009 | Saitoh et al. |
| 2009/0093453 A1 | 4/2009 | Iwakami et al. |
| 2009/0111992 A1 | 4/2009 | Saitoh et al. |

FOREIGN PATENT DOCUMENTS

| EP | 1 437 353 A1 | 7/2004 |
| EP | 1 614 419 A1 | 1/2006 |
| JP | 60-36481 | 2/1985 |
| JP | 4-182463 | 6/1992 |
| JP | 5-140086 | 6/1993 |
| JP | 5-178816 | 7/1993 |
| JP | 5-294922 | 11/1993 |
| JP | 8-143533 | 6/1996 |
| JP | 11-12238 | 1/1999 |
| JP | 11-43455 | 2/1999 |
| WO | 98/43957 | 10/1998 |
| WO | 99/31056 | 6/1999 |
| WO | 02/100850 | 12/2002 |
| WO | 03/035647 | 5/2003 |
| WO | 2004/091605 | 10/2004 |
| WO | 2005/012291 | 2/2005 |
| WO | 2005/019200 | 3/2005 |

OTHER PUBLICATIONS

U.S. Appl. No. 13/008,982, filed Jan. 19, 2011, Kimura, et al.
Edited by CSJ, "Shin Jikken Kagaku Koza 14 Yuki Kagobatsu no Gosei to Hanno II", The Chemical Society of Japan, Maruzen, pp. 947-950, 1977.
Leardini, Rino et al., "Synthesis and Rearrangement of Diaryl-Benzo[b]Thiophenes, A New Synthesis of 2,3-Diaryl-Benzo[b]Thiophens", Tetrahedron Letters, vol. 24, No. 32, pp. 3381-3382, 1983.
Matsuki, Yasuo et al. "Shuka thianaphthenyl Magnesium to Nisanka Tanso tono Hanno", Nippon Kagaku Zasshi, vol. 88 No. 4, pp. 445-447, 1967.
MacDowell, D. W. H. et al, "A Synthesis of 7-Substituted Benzo[b]thiophene Derivatives", J. Heterocycl. Chem., vol. 2, pp. 44-48, 1965.
Prasad, A.S. Bhanu et al., "Convenient Methods for the Reduction of Amides, Nitriles, Carboxylic Esters, Acids and Hydroboration of Alkenes Using $NaBH_4/I_2$System", Tetrahderon, vol. 48, No. 22, pp. 4623-4628, 1992.
Mitsumori, Susumu et al., "Synthesis and Biological Activity of Various Derivatives of a Novel Class of Potent, Selective, and Orally Active Prostaglandin $D_2$ Receptor antagonists. 2. 6,6-Dimethylbicyclo[3.1.1]heptane Derivatives", J. Med. Chem., vol. 46, pp. 2446-2455, 2003.
Iwatsuki, Shouji et al., "Preparation of 4, 7-Bis[cyano(ethoxycarbonyl)methylene]-4, 7-dihydrobenzofuran, 4,7-Bis [cyano(ethoxycarbonyl)methylene]-4, 7, -dihydrobenzothiophene, and 11,12-Bis(ethoxycarbonyl)-11, 12-dicyano-1, 4-naphthoquinodimethane and Their Polymerization Behavior", Macromolecules, vol. 22, pp. 1014-1021, 1989.

(Continued)

Primary Examiner — Taylor Victor Oh
(74) Attorney, Agent, or Firm — Oblon, Spivak, McClelland, Maier & Neustadt, L.L.P.

(57) ABSTRACT

A Process for production of 1-(3-(2-(1-benzothiophen-5-yl) ethoxy)propyl)azetidin-3-ol or salts thereof which comprises using as a starting compound as a (phenylthio)acetic acid derivative or salts thereof represented by the general formula:

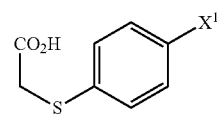

wherein $X^1$ represents a halogen atom,
is useful as a safe process for mass production of 1-(3-(2-(1-benzothiophen-5-yl)ethoxy)propyl)azetidin-3-ol or salts thereof which is useful as a remedy for disease of central and peripheral nerve.

14 Claims, No Drawings

OTHER PUBLICATIONS

Nussbaumer, P. et al., "Synthesis and Structure-Activity Relationships of Benzo[b]thienylallylamine Antimycotics", J. Med. Chem., vol. 34, pp. 65-73, 1991.

Meyer, Michael D. et al., "Structure-Activity Studies for a Novel Series of N-(Arylethyl)-N-(1,2,3,4-tetrahydronaphthalen-1-ylmethyl)-N-methylamines Possessing Dual 5-HT uptake Inhibiting and $\alpha_2$-Antagonistic Activities", Journal of Medicinal Chemistry, vol. 40, No. 7, pp. 1049-1062, 1997.

Gordon W. Gribble "Sodium boroydride in carboxylic acid media: a phemomenal reduction system" Chemical Society Reviews, vol. 27, XP007908370, 1998, pp. 395-404.

H.G. Weiss, et al., "Diborane from the Sodium Borohydride-Sulfuric Acid Reaction", Journal of the Americal Chemical Society, vol. 81, XP-002595830, Dec. 5, 1959, pp. 6167-6168.

U.S. Appl. No. 13/327,152, filed Dec. 15, 2011, Saitoh, et al.

Edited by CSJ, "Shin Jikken Kagaku Koza 14 Yuki Kagobutsu no Gosei to Hanno III", The Chemical Society of Japan, Maruzen, pp. 1599-1601, 1978.

PROCESS FOR PRODUCTION OF 1-(3-(2-(1-BENZOTHIOPHEN-5-YL)-ETHOXY)PROPYL)AZETIDIN-3-OL OR SALTS THEREOF

CROSS REFERENCE TO RELATED APPLICATION

The present application is divisional application of U.S. application Ser. No. 11/909,809, with a 371(c) date of Sep. 27, 2007, which is the national stage of international application PCT/JP2006/306127, filed on Mar. 27, 2006, the text of which is incorporated herein in its entirety by reference, and claiming the benefit of the filing date of Japanese Applications No. 2005-090831, filed on Mar. 28, 2005, No. 2005-174738, filed Jun. 15, 2005, No. 2005-206808, filed Jul. 15, 2005, and No. 2005-230666, filed Aug. 9, 2005, the texts of which are incorporated by reference.

FIELD OF THE INVENTION

The present invention relates to a new process for production of 1-(3-(2-(1-benzothiophen-5-yl)ethoxy)propyl)azetidin-3-ol or salts thereof which is useful as remedies for central nervous system and peripheral nerve diseases.

BACKGROUND ART 1-(3-(2-(1-benzothiophen-5-yl)ethoxy)propyl)azetidin-3-ol or salts thereof has nerve protective action, nerve regeneration promotion action and neurite outgrowth action, and is a useful compound as remedies for central nervous system and peripheral nerve diseases.

As processes for production of this compound, for example, (1) a process of reacting 5-(2-(3-chloropropoxy)ethyl)-1-benzothiophene with 3-azetidinol or salts thereof, (2) a process of subjecting 1-(3-(2-(1-benzothiophen-5-yl)ethoxy) propionyl)azetidin-3-ol obtained from 3-(2-(1-benzothiophen-5-yl)ethoxy)propionic acid or its salts thereof to reduction reaction with borane-tetrahydrofuran complex or subjecting it to reduction reaction with sodium borohydride in the presence of boron trifluoride complex tetrahydrofuran complex, and so forth are known (patent document 1).

However, the process of (1) has the following defects, (A) the yield is low, (B) complicated procedures of purification such as silica gel column chromatography are necessary, (C) therefore, a lot of waste is egested, and so forth.

In addition, the process of (2) cannot be satisfied as an industrial manufacturing process, because the process has the following defects, (A) the process uses reagents of borane-tetrahydrofuran complex and boron trifluoride tetrahydrofuran and so forth, which are harmful to human body, highly flammable, highly toxic and having problems of stability, (B) therefore, attention is necessary to handle and store it and special equipments are required, and so forth.

In addition, as a process for production of 3-(2-(1-benzothiophen-5-yl)ethoxy)propionic acid or salts thereof used in (2) mentioned above, for example, the following processes are known, (3) a process of subjecting 2-(1-benzothiophen-5-yl)ethanol to Michael addition reaction with tert-butyl acrylate, subsequently subjecting it to de-tert-butylation, (4) a process of subjecting 2-(1-benzothiophen-5-yl)ethanol to Michael addition reaction with acrylonitrile, subsequently subjecting it to hydrolysis with acid, and so forth (patent document 1).

However, the processes of (3) and (4) cannot be satisfied as industrial manufacturing processes, because these processes have the following defects, the process of (3): (A) by-products form because of the occurrence of trans-esterification of acrylic acid, (B) special equipments and treatments are required because of the occurrence of a large quantity of combustible isobutene gas in de-tert-butylation reaction, the process of (4): the yield of hydrolysis with acid is low, and so forth.

As a process for production of 2-(1-benzothiophen-5-yl)ethanol used in (3) and (4) mentioned above, for example, the following processes are known, (5) a process of subjecting 5-methyl-1-benzothiophene to bromination with N-bromosuccinimide and to reaction with cyano compounds to obtain (1-benzothiophen-5-yl)acetonitrile, subsequently subjecting it to hydrolysis, subsequently subjecting it to reduction reaction (non-patent document 1, 2, 3), (6) a process of reacting 5-bromo-1-benzothiophene with magnesium to obtain Grignard reagent, subsequently subjecting it to reaction with ethylene oxide (patent document 2), (7) a process of subjecting 5-(1-benzothiophene)carbaldehyde to Wittig reaction with methoxymethylene ylide, subsequently subjecting it to hydrolysis to obtain (1-benzothiophen-5-yl)acetaldehyde, subsequently subjecting it to reduction reaction, and so forth (patent document 3).

However, the processes of (5) to (7) cannot be satisfied as industrial manufacturing processes, because these processes have the following defects, (A) intermediates have a stimulatory property, (B) a highly toxic reagent (cyano compounds) is used, (C) a carcinogenic reagent (ethylene oxide) is used, (D) highly ignitable reagents (butyllithium, Grignard reagent) are used, (E) procedures of the reaction are complicated, and so forth.

On the other hand, as processes for production of benzothiopheneacetic acid derivative or salts thereof, for example, the following processes are known, (8) a process of subjecting the hydroxyl group of benzothiophenemethanol to halogenation, subsequently subjecting it to reaction with cyano compounds to obtain benzothiopheneacetonitrile, subsequently subjecting it to hydrolysis (non-patent document 3), (9) a process of subjecting 7-oxo-4,5,6,7-tetrahydrobenzothiophene produced from 3-bromothiophene to Reformatsky reaction with ethyl bromoacetate, subsequently subjecting it to aromatization by dehydrogenation by use of sulfur, and subjecting it to hydrolysis, and so forth (non-patent document 4).

However, the processes of (8) and (9) cannot be satisfied as industrial manufacturing processes, because these processes have the following defects, (A) intermediates have a stimulatory property, (B) a highly toxic reagent (cyano compounds) is used, (C) therefore, complicated treatments of waste are required, (D) there are many steps of the process (E) the yield is low, (F) the reaction temperature is high, (G) procedures of the reaction are complicated, and so forth.

In addition, as a process for production of 5-halogeno-1-benzothiophene derivative, for example, the following processes are known, (10) a process of reacting 4-halogenothiophenol with 2-halogenoacetaldehyde dimethylacetal in the presence of base to obtain 2-(4-halogenophenylthio)acetaldehyde dimethylacetal, subsequently subjecting it to intramolecular ring closure reaction in the presence of polyphosphoric acid, and so forth (non-patent document 5, patent document 4, patent document 5).

However, the process of (10) cannot be satisfied as an industrial manufacturing process, because the process has the following defects, (A) complicated procedures such as distillation or silica gel column chromatography and so forth are necessary to isolated because the production intermediates are oily substances, (B) treatments of the process are complicated in ring closure reaction by use of phosphate compound because complicated by-products form, (C) complicated procedures such as distillation or silica gel column chromatography and so forth are necessary to separate 5-halogeno-1-benzothiophene derivatives from formed by-products because their derivatives have low melting points, (D) a large quantities of liquid waste is formed, which contains phosphorus compounds that require complicated procedures for treatment, and so forth.

As 4-halogenothiophenol used in (10) mentioned above, for example, (11) a process of subjecting thioanisole to halogenation with chlorine or bromine, subsequently subjecting it to demethylation with large excess of chlorine (patent document 6), (12) a process of reacting (4-halogenophenylthio) acetic acid with sodium sulfide in the presence of sodium hydroxide (patent document 7), (13) a process of reacting monohalogenobenzene with sulfur monochloride in the presence of zinc chloride to obtain dihalogenodiphenyl polysulfide, subsequently subjecting it to reduction reaction with hydrochloric acid-zinc (patent document 8), (14) a process of reacting 1,4-dihalogenobenzene with sodium hydrosulfide in 1-methyl-2-pyrrolidone (patent document 9), and so forth are known.

However, the processes of (11) to (14) cannot be satisfied as industrial manufacturing processes, because these processes have the following defects, (A) the yield is low, (B) isomers form, (C) high reaction temperature is required, (D) reagents that bear large environment loads such as chlorine or sulfide are used, and so forth.

Further, as a process for production of a benzothiophene derivative from a (phenylthio)acetic acid derivative or salts thereof, for example, the following processes are known, (15) a process of subjecting it to intramolecular ring closure reaction in the presence of Lewis acid, subsequently subjecting it to reduction reaction, subsequently subjecting it to dehydration reaction, and so forth (patent document 10).

However, in this process, the structure of produced compound is limited.

[Patent Document 1]
International publication No. 03/035,647 pamphlet
[Patent Document 2]
EP0129478 bulletin
[Patent Document 3]
International publication No. 99/31,056 pamphlet
[Patent Document 4]
International publication No. 02/100,850 pamphlet
[Patent Document 5]
International publication No. 2,005/012,291 pamphlet
[Patent Document 6]
Japanese Patent Laid-Open No. H08-143533 bulletin
[Patent Document 7]
Japanese Patent Laid-Open No. H05-178816 bulletin
[Patent Document 8]
Japanese Patent Laid-Open No. H05-140086 bulletin
[Patent Document 9]
Japanese Patent Laid-Open No. H04-182463 bulletin
[Patent Document 10]
International publication No. 98/43,967 pamphlet
[Non-Patent Document 1]
Journal of Medicinal Chemistry (J. Med. Chem.), 1991, Vol. 34, p. 65-73
[Non-Patent Document 2]
Journal of Medicinal Chemistry (J. Med. Chem.), 1997, Vol. 40, p 1049-1062
[Non-Patent Document 3]
Nippon Kagaku Zashi, 1967, Vol. 88, p. 445-447
[Non-Patent Document 4]
Journal of Heterocyclic Chemistry (J. Heterocyclic Chem.), 1965, Vol. 2, p. 44-48
[Non-Patent Document 5]
Journal of Medicinal Chemistry (J. Med. Chem.), 2003, Vol. 46, p 2446-2455

DISCLOSURE OF THE INVENTION

Problem to be Solved by the Invention

A new process for production of 1-(3-(2-(1-benzothiophen-5-yl)ethoxy)propyl)azetidin-3-ol and salts thereof, process which has safety to human body, low environmental loads and a possibility of mass production, is strongly expected.

Means to Solve the Problem

Under the circumstances, the present inventors have studied zealously and consequently, and found that in a process for production of 1-(3-(2-(1-benzothiophen-5-yl)ethoxy)propyl)azetidin-3-ol or salts thereof from 2-(1-benzothiophen-5-yl)ethanol, a process for production of 3-(2-(1-benzothiophen-5-yl)ethoxy)propionic acid or salts thereof characterized by subjecting 2-(1-benzothiophen-5-yl)ethanol to Michael addition reaction with acrylonitrile in the presence of base, subsequently subjecting it to reaction with an alcohol represented by the general formula [1]:

$$R^1CH_2OH \qquad [1]$$

wherein $R^1$ represents a hydrogen atom or an unsubstituted or substituted alkyl, cycloalkyl or aryl group,
in the presence of acid to obtain a propionic acid ester derivative represented by the general formula [2]:

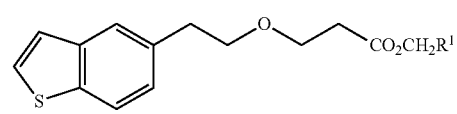

wherein $R^1$ has the same meanings as the above, subsequently subjecting the propionic acid ester derivative to hydrolysis reaction in the presence of base;
the propionic acid ester derivative represented by the general formula [2]:

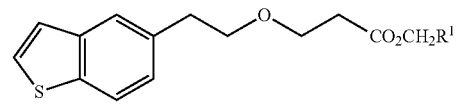

wherein $R^1$ has the same meanings as the above, being important intermediates in the production of 3-(2-(1-benzothiophen-5-yl)ethoxy)propionic acid or salts thereof;
a process for production of 1-(3-(2-(1-benzothiophen-5-yl) ethoxy)propionyl)azetidin-3-ol or salts thereof characterized by deriving 3-(2-(1-benzothiophen-5-yl)ethoxy)propionic acid or salts thereof to a reactive derivative, subsequently reacting the reactive derivative with 3-azetidinol or salts thereof in the presence of base, and subsequently crystallizing the crystals from the reaction mixture;
a process for production of 1-(3-(2-(1-benzothiophen-5-yl) ethoxy)propyl)azetidin-3-ol or salts thereof characterized by subjecting 1-(3-(2-(1-benzothiophen-5-yl)ethoxy)propionyl)azetidin-3-ol to reduction reaction with an addition of activator in the presence of alkali metal borohydride; and a process for production of 1-(3-(2-(1-benzothiophen-5-yl) ethoxy)propyl)azetidin-3-ol or salts thereof characterized by subjecting 2-(1-benzothiophen-5-yl)ethanol to Michael addition reaction with acrylonitrile in the presence of base, subsequently subjecting it to reaction with an alcohol represented by the general formula [1]:

  [1]

wherein $R^1$ has the same meanings as the above, in the presence of acid to obtain a propionic acid ester derivative represented by the general formula [2]:

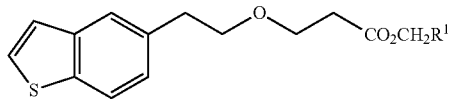  [2]

wherein $R^1$ has the same meanings as the above, subsequently subjecting the propionic acid ester derivatives to hydrolysis reaction in the presence of base to obtain 3-(2-(1-benzothiophen-5-yl)ethoxy)propionic acid or salts thereof, subsequently converting it to a reactive derivative, subsequently reacting the reactive derivative with 3-azetidinol or salts thereof in the presence of base to obtain 1-(3-(2-(1-benzothiophen-5-yl)ethoxy)propionyl)azetidin-3-ol, subsequently subjecting it to reduction reaction with an addition of activator in the presence of alkali metal borohydride.

In addition, the present inventors have found that in the process of 2-(1-benzothiophen-5-yl)ethanol which is a starting material, a process for production of a 5-halogeno-1-benzothiophene derivative represented by the general formula [6]:

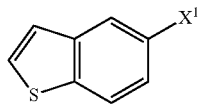  [6]

wherein $X^1$ represents a halogen atom, characterized by reacting a (phenylthio)acetic acid derivative or salts thereof represented by the general formula [3]:

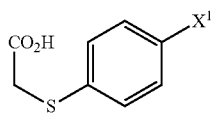  [3]

wherein $X^1$ has the same meanings as the above, with a halogenating agent to obtain an acid halide represented by the general formula [4]:

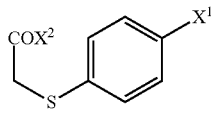  [4]

wherein $X^2$ represents a halogen atom; $X^1$ has the same meanings as the above, subsequently subjecting the acid halide to intramolecular ring closure reaction in the presence of Lewis acid, subsequently subjecting it to reduction reaction to obtain a dihydrobenzothiophene derivative represented by the general formula [5]:

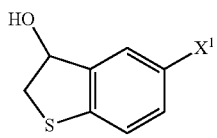  [5]

wherein $X^1$ has the same meanings as the above, and subjecting the dihydrobenzothiophene derivative to dehydration reaction in the presence of acid catalyst; the dihydrobenzothiophene derivative represented by the general formula [5]:

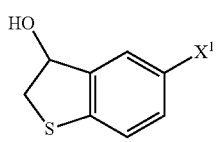  [5]

wherein $X^1$ has the same meanings as the above, being important intermediates in the process for production of a 5-halogeno-1-benzothiophene derivative represented by the general formula [6]:

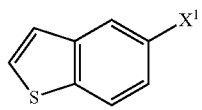  [6]

wherein $X^1$ has the same meanings as the above; the 5-halogeno-1-benzothiophene derivative represented by the general formula [6]:

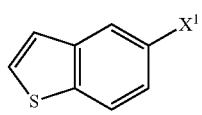  [6]

wherein $X^1$ has the same meanings as the above, can be produced at simple procedures with a high purity by crystallizing and isolating crystals of the dihydrobenzothiophene derivative represented by the general formula [5]:

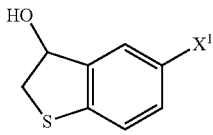

wherein $X^1$ has the same meanings as the above, subsequently subjecting the crystals to dehydration reaction;

a process for production of benzothiophene derivative or salts thereof represented by the general formula [9]:

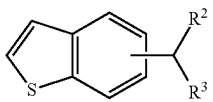

wherein $R^2$ and $R^3$ represent identically or differently an unsubstituted or substituted alkyloxycarbonyl, cycloalkyloxycarbonyl or aralkyloxycarbonyl group or cyano group, characterized by coupling a benzothiophene derivative represented by the general formula [7]:

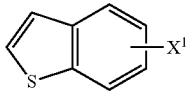

wherein $X^1$ has the same meanings as the above, in the presence of base and palladium catalyst with a malonic acid derivative or salts thereof represented by the general formula [8]

wherein $R^2$ and $R^3$ have the same meanings as the above; a process for production of benzothiopheneacetic acid derivative or salts thereof represented by the general formula [10]:

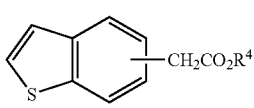

wherein $R^4$ represents a hydrogen atom or unsubstituted or substituted alkyl, cycloalkyl or aralkyl group, characterized by reacting a benzothiophene derivative or salts thereof represented by the general formula [9]

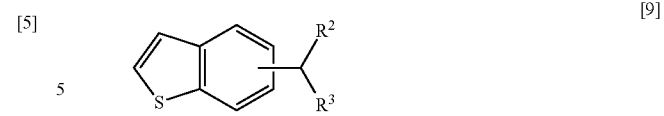

wherein $R^2$ and $R^3$ have the same meanings as the above, with acid or base, subjecting the benzothiophene derivative or salts thereof to decarboxylation reaction if necessary;

the benzothiophene derivative represented by the general formula [9]:

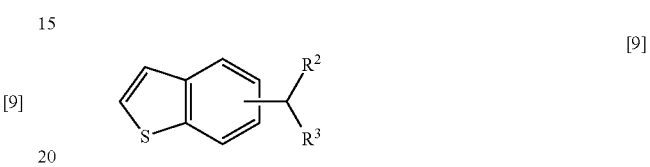

wherein $R^2$ and $R^3$ have the same meanings as the above, being important intermediates in the process for production of benzothiopheneacetic acid derivative or salts thereof represented by the general formula [10]:

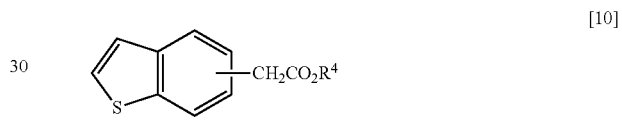

wherein $R^4$ has the same meanings as the above;

a process for production of 2-(1-benzothiophen-5-yl)ethanol characterized by subjecting a benzothiopheneacetic acid derivative or salts thereof represented by the general formula [11]:

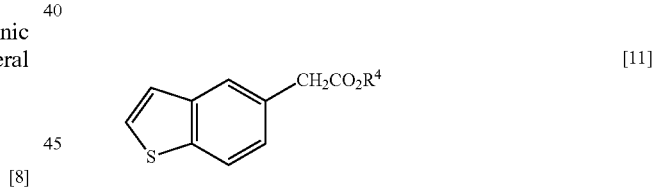

wherein $R^4$ has the same meanings as the above, to hydrolysis reaction if necessary, subsequently subjecting it to reductive reaction with an addition of activator in the presence of alkali metal borohydride; and a process for production of 2-(1-benzothiophen-5-yl)ethanol characterized by reacting a (phenylthio)acetic acid derivative or salts thereof represented by the general formula [3]:

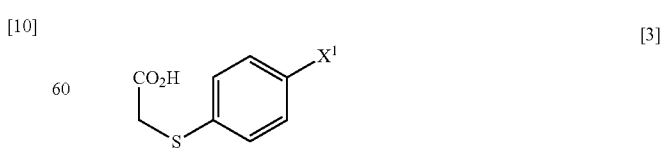

wherein $X^1$ has the same meanings as the above, with a halogenating agent to obtain an acid halide represented by the general formula [4]:

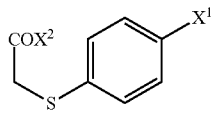  [4]

wherein $X^1$ and $X^2$ have the same meanings as the above, subsequently subjecting the acid halide to intramolecular ring closure reaction in the presence of Lewis acid, subsequently subjecting it to reduction reaction to obtain a dihydrobenzothiophene derivative represented by the general formula [5]:

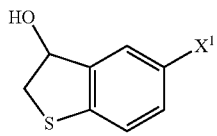  [5]

wherein $X^1$ has the same meanings as the above, subsequently subjecting the dihydrobenzothiophene derivative to dehydration reaction in the presence of acid catalyst to obtain a 5-halogeno-1-benzothiophene derivative represented by the general formula [6]:

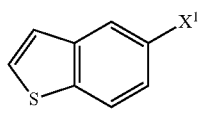  [6]

wherein $X^1$ has the same meanings as the above, subsequently coupling the 5-halogeno-1-benzothiophene derivative with a malonic acid derivative or salts thereof represented by the general formula [8]:

  [8]

wherein $R^2$ and $R^3$ have the same meanings as the above, in the presence of base and palladium catalyst to obtain a benzothiophene derivative or salts thereof represented by the general formula [12]:

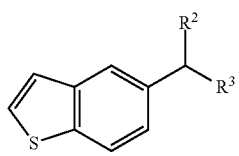  [12]

wherein $R^2$ and $R^3$ have the same meanings as the above, subsequently reacting the benzothiophene derivative or salts thereof with acid or base, subjecting it to decarboxylation reaction if necessary, to obtain a benzothiopheneacetic acid derivative or salts thereof represented by the general formula [11]:

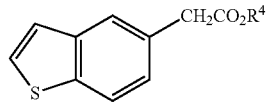  [11]

wherein $R^4$ has the same meanings as the above, subsequently subjecting, the benzothiopheneacetic acid derivative or salts thereof to hydrolysis reaction if necessary, subsequently subjecting it to reduction reaction with an addition of activator in the presence of alkali metal borohydride.

Further, the present inventors have found that a process for production of 1-(3-(2-(1-benzothiophen-5-yl) ethoxy)propyl)azetidin-3-ol or salts thereof characterized by reacting a (phenylthio)acetic acid derivative or salts thereof represented by the general formula [3]:

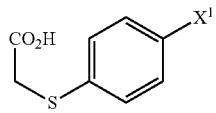  [3]

wherein $X^1$ has the same meanings as the above, with a halogenating agent to obtain an acid halide represented by the general formula [4]:

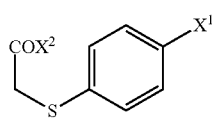  [4]

wherein $X^1$ and $X^2$ have the same meanings as the above, subsequently subjecting the acid halide to intramolecular ring closure reaction in the presence of Lewis acid, subsequently subjecting it to reduction reaction to obtain a dihydrobenzothiophene derivative represented by the general formula [5]:

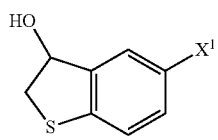  [5]

wherein $X^1$ has same the meanings as the above, subsequently subjecting the dihydrobenzothiophene derivative to dehydration reaction in the presence of acid catalyst to obtain a 5-halogeno-1-benzothiophene derivative represented by the general formula [6]:

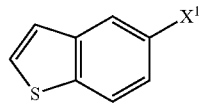  [6]

wherein $X^1$ has the same meanings as the above, subsequently coupling the 5-halogeno-1-benzothiophene derivative with a malonic acid derivative or salts thereof represented by the general formula [8]:

[8]

wherein $R^2$ and $R^3$ have same meanings as the above, in the presence of base and palladium catalyst to obtain a benzothiophene derivative or salts thereof represented by the general formula [12]:

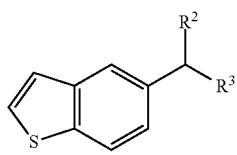
[12]

wherein $R^2$ and $R^3$ have the same meanings as the above, subsequently reacting the benzothiophene derivative or salts thereof with acid or base, subjecting it to decarboxylation reaction if necessary, to obtain a benzothiopheneacetic acid derivative or salts thereof represented by the general formula [11]:

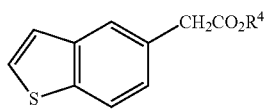
[11]

wherein $R^4$ have the same meanings as the above, subsequently subjecting the benzothiopheneacetic acid derivative or salts thereof to hydrolysis reaction if necessary, subsequently subjecting it to reduction reaction with an addition of activator in the presence of alkali metal borohydride to obtain 2-(1-benzothiophen-5-yl)ethanol, subsequently subjecting 2-(1-benzothiophen-5-yl)ethanol to Michael addition reaction with acrylonitrile in the presence of base, subsequently subjecting it to reaction with an alcohol represented by the general formula [1]:

$R^1CH_2OH$ [1]

wherein $R^1$ has the same meanings as the above,
in the presence of acid to obtain a propionic acid ester derivative represented by the general formula [2]:

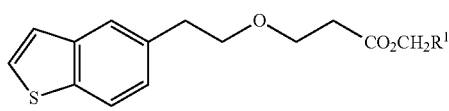
[2]

wherein $R^1$ has the same meanings as the above, subsequently subjecting the propionic acid ester derivative to hydrolysis reaction in the presence of base to obtain 3-(2-(1-benzothiophen-5-yl)ethoxy)propionic acid or salts thereof, subsequently converting 3-(2-(1-benzothiophen-5-yl)ethoxy)propionic acid or salts thereof to a reactive derivative, subsequently reacting the reactive derivative with 3-azetidinol or salts thereof in the presence of base to obtain 1-(3-(2-(1-benzothiophen-5-yl)ethoxy)propionyl)azetidin-3-ol, and subsequently subjecting 1-(3-(2-(1-benzothiophen-5-yl)ethoxy)propionyl)azetidin-3-ol to reduction reaction with an addition of activator in the presence of alkali metal borohydride, and have completed the present invention.

Effect of the Invention

The process for production of 1-(3-(2-(1-benzothiophen-5-yl)ethoxy)propyl)-3-azetidinol or salts thereof of the present invention has the following characteristics, (1) the yield is high, (2) silica gel column chromatography is not required, (3) therefore, the amount of wastes is small, (4) reagents which have harmfulness and problems of stability are not used, and so forth, and the process is useful as industrial manufacturing process.

The process for production of 3-(2-(1-benzothiophen-5-yl)ethoxy)propionic acid or salts thereof of the present invention has the following characteristics, (1) by-products are small, (2) inflammable gases do not occur, (3) the yield is high, and so forth, and the process is useful as industrial manufacturing process.

The process for production of benzothiopheneacetic acid derivative or salts thereof represented by the general formula [10] of the present invention has the following characteristics, (1) stimulative intermediates are not used during the process, (2) highly toxic reagents (cyano compounds) are not used, (3) complicated treatments of waste are not required, (4) the number of steps of the process is few, (5) the yield is high, (6) high reaction temperature is not required, (7) reaction procedures are simple, and so forth, and the process is useful as industrial manufacturing process.

The process for production of 5-halogeno-1-benzothiophene derivatives represented by the general formula [6] of the present invention has the following characteristics, (1) by-products are few, (2) purification can be performed by simple procedure such as extraction and crystallization, (3) therefore, complicated refining procedures such as distillation or silica gel column chromatography are not required, and so forth, and the process is useful as industrial manufacturing process.

BEST MODE FOR CARRYING OUT THE INVENTION

The present invention is explained below in detail.
In the present specification, unless otherwise specified, the term "halogen atom" means fluorine atom, chlorine atom, bromine atom or iodine atom;
the term "alkyl group" means a straight or branched chain $C_{1-12}$alkyl group, for example, methyl, ethyl, propyl, isopropyl, butyl, sec-butyl, isobutyl, tert-butyl, pentyl, isopentyl, hexyl, heptyl, octyl or the like;
the term "cycloalkyl group" means a $C_{3-8}$cycloalkyl group, for example, cyclopropyl, cyclobutyl, cyclopentyl, cyclohexyl or the like;
the term "aralkyl group" means an ar$C_{1-8}$alkyl group, for example, benzyl, diphenylmethyl, trityl, phenethyl, naphthylmethyl or the like;
the term "alkoxy group" means a straight or branched chain $C_{1-6}$alkyloxy group, for example, methoxy, ethoxy, propoxy, isopropoxy, butoxy, isobutoxy, sec-butoxy, tert-butoxy, pentyloxy, isopentyloxy or the like;

the term "alkyloxycarbonyl group" means a straight or branched chain $C_{1-12}$alkyloxycarbonyl group, for example, methoxycarbonyl, ethoxycarbonyl, 1,1-dimethylpropoxycarbonyl, isopropoxycarbonyl, 2-ethylhexyloxycarbonyl, tert-butoxycarbonyl, tert-pentyloxycarbonyl or the like;

the term "cycloalkyloxycarbonyl group" means a $C_{3-8}$cycloalkyloxycarbonyl group, for example, cyclopropoxycarbonyl, cyclobutoxycarbonyl, cyclopentyloxycarbonyl, cyclohexyloxycarbonyl or the like;

the term "aralkyloxycarbonyl group" means an ar$C_{1-6}$alkyloxycarbonyl group, for example, benzyloxycarbonyl, phenethyloxycarbonyl or the like;

the terms "aryl group" means group, for example, phenyl, naphthyl or the like;

the term "alkenyl group" means a $C_{2-12}$alkenyl group, for example, vinyl, propenyl, butenyl, pentenyl, hexenyl, heptenyl, octenyl or the like, respectively.

The alkyl, cycloalkyl and aryl group of $R^1$ may be substituted with at least one group selected from a halogen atom, a hydroxyl group, a nitro group, an alkyl group, a cycloalkyl group, an alkoxy group, an alkenyl group and an aryl group or the like.

The alkyloxycarbonyl, cycloalkyloxycarbonyl and aralkyloxycarbonyl group of $R^2$ and $R^3$ may be substituted with at least one group selected from a halogen atom, a hydroxyl group, a nitro group, an alkyl group, a cycloalkyl group, an alkoxy group, an alkenyl group and an aryl group or the like.

The alkyl, cycloalkyl and aralkyl group of $R^4$ may be substituted with at least one group selected from a halogen atom, a hydroxyl group, a nitro group, an alkyl group, a cycloalkyl group, an alkoxy group, an alkenyl group and an aryl group or the like.

In the present invention, the following processes are given for preferable manufacturing processes.

For the production of 3-(2-(1-benzothiophen-5-yl)ethoxy)propionic acid or salts thereof, in the process for production by subjecting 2-(1-benzothiophen-5-yl)ethanol to Michael addition reaction in the presence of base with acrylonitrile, subsequently reacting it with an alcohol represented by the general formula [1]:

$$R^1CH_2OH \quad [1]$$

wherein $R^1$ has the same meanings as the above,
in the presence of acid to obtain a propionic acid ester derivative represented by the general formula [2]:

[2]

wherein $R^1$ has the same meanings as the above,
and subjecting the propionic acid ester derivative to hydrolysis reaction in the presence of base, the process for production in which $R^1$ is a hydrogen atom or an alkyl group is preferable, the process for production in which $R^1$ is a hydrogen atom, methyl group, ethyl group or propyl group is more preferable, and the process for production in which $R^1$ is a hydrogen atom or ethyl group is further more preferable.

The process for production in which the acid used is an inorganic acid is preferable, and the process for production in which the acid used is sulfuric acid or hydrogen chloride is more preferable.

In the case that the acid is hydrogen chloride, the process for production in which $R^1$ is hydrogen atom is preferable.

In the case that the acid is sulfuric acid, the process for production in which $R^1$ is ethyl group is preferable.

In the process for production of 1-(3-(2-(1-benzothiophen-5-yl)ethoxy)propyl)azetidin-3-ol or salts thereof by subjecting 1-(3-(2-(1-benzothiophen-5-yl)ethoxy)propionyl)azetidin-3-ol to reduction reaction with an addition of activator in the presence of alkali metal borohydride, the process for production in which the alkali metal borohydride used is sodium borohydride is preferable.

The process for production in which the activator used is a protonic acid such as sulfuric acid and hydrogen chloride and so forth is preferable, and the process for production in which the activator used is sulfuric acid is more preferable.

In the case that the activator is sulfuric acid, the process for production in which the volume of sulfuric acid used is 0.5-0.6 times mole per mole of the alkali metal borohydride, the addition of sulfuric acid at 0 to 30° C. for 10 minutes to 6 hours and the subsequent reaction at 30 to 70° C. is preferable.

For the production of a dihydrobenzothiophene derivative represented by the general formula [5]:

[5]

wherein $X^1$ has the same meanings as the above,
in the process for production by reacting a (phenylthio)acetic acid derivative or salts thereof represented by the general formula [3]:

[3]

wherein $X^1$ has the same meanings as the above,
with a halogenating agent to obtain an acid halide represented by the general formula [4]:

[4]

wherein $X^1$ and $X^2$ have the same meanings as the above, subsequently subjecting the acid halide to intramolecular ring closure reaction in the presence of Lewis acid, subsequently subjecting it to reduction reaction, the process for production in which $X^1$ is a chlorine atom, a bromine atom or an iodine atom is preferable, the process for production in which $X^1$ is a bromine atom or an iodine atom is more preferable, and the process for production in which $X^1$ is a bromine atom is further more preferable.

For the production of a 5-halogeno-1-benzothiophene derivative represented by the general formula [6]:

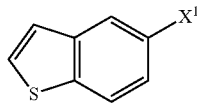

wherein $X^1$ has the same meanings as the above, in the process for production by subjecting a dihydrobenzothiophene derivative represented by the general formula [5]:

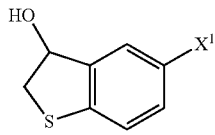

wherein $X^1$ has the same meanings as the above, to dehydration reaction in the presence of acid catalyst, the process for production in which $X^1$ is a chlorine atom, a bromine atom or an iodine atom is preferable, the process for production in which $X^1$ is a bromine atom or an iodine atom is more preferable, and the process for production in which $X^1$ is a bromine atom is further more preferable.

In the process for isolation by crystallizing crystals of a dihydrobenzothiophene derivative represented by the general formula [5], the process for isolation by crystallizing it from an aliphatic hydrocarbon such as hexane and cyclohexane and so forth is preferable, the process for isolation by crystallizing it from hexane or cyclohexane is more preferable, and the process for isolation by crystallizing it from cyclohexane is further more preferable.

In the production of benzothiophene derivative or salts thereof represented by the general formula [9]:

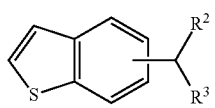

wherein $R^2$ and $R^3$ have the same meanings as the above, the process for production by subjecting a benzothiophene derivative represented by the general formula [7]:

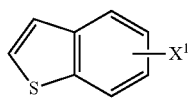

wherein $X^1$ has the same meanings as the above, to coupling reaction with a malonic acid derivative or salts thereof represented by the general formula [8a] in the presence of the palladium catalyst and base:

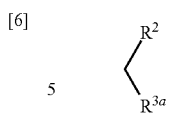

wherein $R^{3a}$ represents an unsubstituted or substituted alkyloxycarbonyl, cycloalkyloxycarbonyl or aralkyloxycarbonyl group; $R^2$ has same meanings as the above, is preferable, the process for production in which $R^2$ is an alkyloxycarbonyl group, an aralkyloxycarbonyl group or a cyano group; $R^{3a}$ is an alkyloxycarbonyl group or an aralkyloxycarbonyl group is more preferable, the process for production in which $R^2$ is a $C_{1-4}$alkyloxycarbonyl group, an ar$C_{1-4}$alkyloxycarbonyl group or a cyano group; $R^{3a}$ is a $C_{1-4}$alkyloxycarbonyl group or an ar$C_{1-4}$alkyloxycarbonyl group is further preferable.

The process for production in which $X^1$ is a chlorine atom, a bromine atom or an iodine atom is preferable, and the process for production in which $X^1$ is a bromine atom or an iodine atom is further preferable.

The process for production in which $X^1$ bonds to 4- or 5-position of the benzothiophene ring is preferable, and the process for production in which $X^1$ bonds 5-position of the benzothiophene ring is further preferable.

In the process for production of a benzothiopheneacetic acid derivative or salts thereof represented by the general formula [10]:

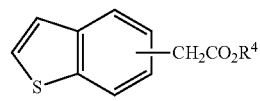

wherein $R^4$ has the same meanings as the above, the process for production by reacting a benzothiophene derivative or salts thereof represented by the general formula [9a]:

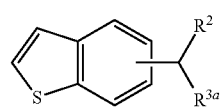

wherein $R^2$ and $R^{3a}$ have the same meanings as the above, with acid or base, subjecting it to decarboxylation reaction if necessary, is preferable, the process for production in which $R^2$ is an alkyloxycarbonyl group, an aralkyloxycarbonyl group or a cyano group; $R^{3a}$ is an alkyloxycarbonyl group or an aralkyloxycarbonyl group is more preferable, and the process for production in which $R^2$ is a $C_{1-4}$alkyloxycarbonyl group, an ar$C_{1-4}$alkyloxycarbonyl group or a cyano group; $R^{3a}$ is a $C_{1-4}$alkyloxycarbonyl group or an ar$C_{1-4}$alkyloxycarbonyl group is further preferable.

The process for production in which the group represented by the general formula:

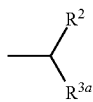

wherein $R^2$ and $R^{3a}$ have the same meanings as the above, bonds to 4- or 5-position of the benzothiophene ring is preferable, and the process for production in which the group bonds to 5-position of the benzothiophene ring is further preferable.

The process for production in which the group represented by the general formula:

—CH$_2$CO$_2$R$^4$ wherein $R^4$ has the same meanings as the above, bonds to 4- or 5-position of the benzothiophene ring is preferable, and the process for production in which the group bonds to 5-position of the benzothiophene ring is further preferable.

The process for production in which $R^4$ is a hydrogen atom or an unsubstituted or substituted alkyl, cycloalkyl or aralkyl group is preferable, the process for production in which $R^4$ is a hydrogen atom, an alkyl group or an aralkyl group is preferable, and the process for production in which $R^4$ is a hydrogen atom, a $C_{1-4}$alkyl group or an ar$C_{1-4}$ alkyl group is further preferable.

In the propionic acid ester derivative represented by the general formula [2]:

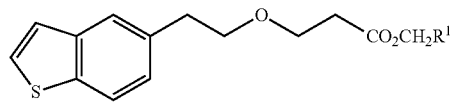

[2]

wherein $R^1$ has the same meanings as the above, the following compounds are given for a preferable compound.

The compound of which $R^1$ is a hydrogen atom or an alkyl group is preferable, the compound of which $R^1$ is a hydrogen atom, a methyl group, an ethyl group or a propyl group is more preferable, and the compound of which $R^1$ is a hydrogen atom or an ethyl group is further preferable.

In a dihydrobenzothiophene derivative represented by the general formula [5]:

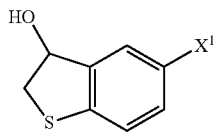

[5]

wherein $X^1$ has the same meanings as the above, the following compounds are given for a preferable compound.

The compound of which $X^1$ is a chlorine atom, a bromine atom or an iodine atom is preferable, the compound of which $X^1$ is a bromine atom or an iodine atom is more preferable, and the compound of which $X^1$ is a bromine atom is further preferable.

In a benzothiophene derivative or salts thereof represented by the general formula [9]:

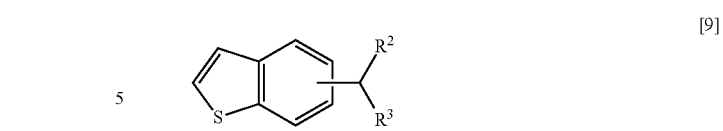

[9]

wherein $R^2$ and $R^3$ have the same meanings as the above, the following compounds are given for a preferable compound.

The compound of which $R^2$ is an alkyloxycarbonyl, cycloalkyloxycarbonyl or aralkyloxycarbonyl group or a cyano group is preferable, the compound of which $R^2$ is an alkyloxycarbonyl group, an aralkyloxycarbonyl group or a cyano group is more preferable, and the compound of which $R^2$ is a $C_{1-4}$alkyloxycarbonyl group, an ar$C_{1-4}$alkyloxycarbonyl group or a cyano group is further preferable.

The compound of which $R^3$ is an alkyloxycarbonyl, cycloalkyloxycarbonyl or aralkyloxycarbonyl group is preferable, the compound of which $R^3$ is an alkyloxycarbonyl group or an aralkyloxycarbonyl group is more preferable, and the compound of which $R^3$ is a $C_{1-4}$alkyloxycarbonyl group or ar$C_{1-4}$alkyloxycarbonyl group is further preferable.

The compound of which the group represented by the general formula:

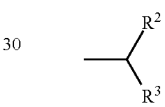

wherein $R^2$ and $R^3$ have the same meanings as the above, bonds to 4- or 5-position of the benzothiophene ring is preferable, and, the compound of which the group bonds to 5-position of the benzothiophene ring is further preferable.

As the representative compound of the general formula [9] or salts thereof of the present invention, for example, the following compounds are given.

In a table, Et represents an ethyl group, $^t$Bu represents a tert-butyl group.

TABLE 1

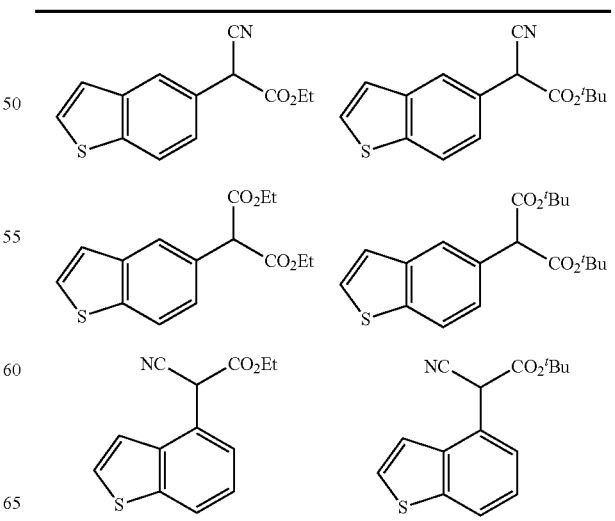

TABLE 1-continued

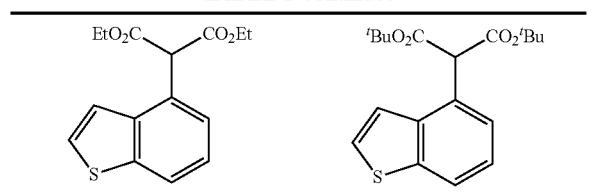

Next, the process for production of the present invention is explained.
[Production Process 1]

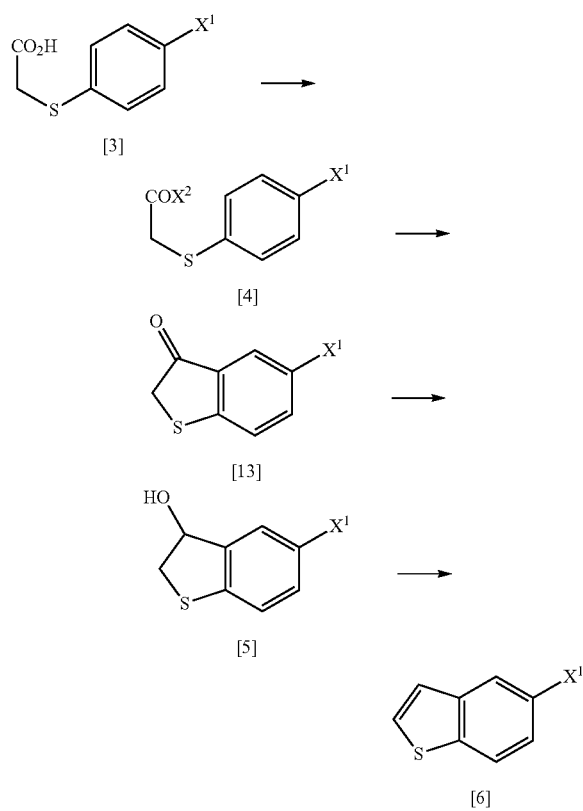

wherein $X^1$ and $X^2$ have the same meanings as the above.

The compound of the general formula [5] can be produced by deriving the compound of the general formula [3] or salts thereof to an acid halide, subsequently subjecting the acid halide to intramolecular ring closure reaction in the presence of Lewis acid, subsequently subjecting it to reduction reaction.

The compound of the general formula [5] can be derived to the compound of general formula [6] easily by subjecting it to dehydration reaction in the presence of acid catalyst.

The compound of the general formula [3] or salts thereof, for example, can be obtained easily and with good yield by reacting thiophenol with chloroacetic acid in the presence of base to obtain (phenylthio)acetic acid, subsequently subjecting (phenylthio)acetic acid to halogenating reaction, or reacting 4-halogenothiophenol with chloroacetic acid in the presence base.

In addition, the salt of the compound of general formula [3], if it is usually known for a salt in acidic group such as carboxyl group, is not particularly limited, but for example, salts with alkali metal such as sodium, potassium, cesium and the like;

salts with alkali earth metal such as calcium, magnesium and the like;
ammonium salts;
and salts with nitrogen containing organic base such as trimethylamine, triethylamine, tributylamine, N,N-diisopropylethylamine, pyridine, N-methylpiperidine, N-methylmorpholine, diethylamine, dicyclohexylamine and the like; are given.

The present process for production is explained below in detail.

Intramolecular Ring Closure Reaction:

The compound of the general formula [13] can be produced by reacting the compound of the general formula [3] or salts thereof with a halogenating agent to obtain an acid halide, subsequently subjecting the acid halide to intramolecular ring closure reaction in the presence of Lewis acid.

This reaction is usually carried out in the presence of solvent, the solvent used, if it does not affect an influence on the reaction, is not particularly limited, for example, aliphatic halogenated hydrocarbons such as dichloromethane, chloroform, dichloroethane and the like;
nitro compounds such as nitromethane, nitrobenzene and the like;
and carbon disulfide and the like; are given, and these solvents may be used in admixture.

As a preferable solvent, aliphatic halogenated hydrocarbons is given, and dichloromethane is more preferable.

The amount of the solvent used is not particularly limited, but is preferably 1 to 50 times volume per weight (v/w) of the compound of the general formula [3] or salts thereof, and is more preferably 3 to 15 times (v/w).

As the halogenating agent used in this reaction, for example, phosphorus oxychloride, phosphorus oxybromide, phosphorus trichloride, phosphorus pentachloride, thionyl chloride, thionyl bromide and oxalyl chloride are given, and thionyl chloride is preferable.

The amount of the halogenating agent used is different in the kind of the halogenating agent, but for example, in the case of thionyl chloride, it may be equal to or more than 0.5 times mole per mole of the compound of the general formula [3] or salts thereof, and is preferably 1 to 2 times mole.

As Lewis acid used in this reaction, for example, aluminum chloride, aluminum bromide, boron trifluoride, titanium tetrachloride, iron chloride, tin chloride, mercuric chloride, sulfuric acid and the like are given, and aluminum chloride is preferable.

The amount of Lewis acid used may be equal to or more than 1 time mole per mole of the compound of general formula [3] or salts thereof, and is preferably 1 to 5 times mole.

The reaction temperature is not particularly limited, but is from −20° C. to equal to or less than the boiling point of solvent, and is preferably 0 to 70° C.

The reaction time is not particularly limited, but is for 10 minutes to 50 hours, and is preferably for 30 minutes to 20 hours.

The compound of the general formula [13] obtained in this way can be isolated and purified, but it is preferable to proceed to the next reaction without isolation.

Reduction Reaction:

The compound of the general formula [5] can be produced by subjecting the compound of the general formula [13] to reduction reaction. This reaction is usually carried out in the presence of solvent, the solvent used, if it does not affect an influence on the reaction, is not particularly limited, but for example, aliphatic halogenated hydrocarbons such as dichloromethane, chloroform, dichloroethane and the like;

ethers such as tetrahydrofuran, 1,2-dimethoxyethane, bis(2-methoxyethyl)ether, dioxane and the like;
amides such as N,N-dimethylformamide, N,N-dimethylacetamide, 1-methyl-2-pyrrolidone and the like;
sulfoxides such as dimethyl sulfoxide and the like;
alcohols such as methanol, ethanol, propanol, 2-propanol, butanol and the like;
nitriles such as acetonitrile and the like;
esters such as methyl acetate, ethyl acetate and the like;
nitro compounds such as nitromethane, nitrobenzene and the like;
aromatic hydrocarbons such as benzene, toluene, xylene and the like;
and water and the like; are given, and these solvents may be used in admixture.

As a preferable solvent, a mixed solvent of aliphatic halogenated hydrocarbons and alcohols are given, a mixed solvent of dichloromethane and methanol is more preferable.

The amount of the solvent used is not particularly limited, but preferably 1 to 50 times volume per weight of the compound of the general formula [13], and is more preferably 3 to 15 times (v/w).

As the reducing agent used in this reaction, for example, alkali metal such as lithium, sodium, potassium and the like;
alkali earth metal such as magnesium, calcium and the like;
metal such as zinc, aluminum, chrome, titanium, iron, samarium, selenium, sodium hydrosulfite and the like, and salts of these metals;
metal hydride such as diisobutylaluminium hydride, trialkylaluminium hydride, stannyl hydride compound, hydrosilane and the like;
complex compound of borohydride such as sodium borohydride, lithium borohydride, potassium borohydride and the like;
complex compound of aluminum hydride such as lithium aluminum hydride and the like;
and borane and alkyl borane and the like; are given.

As a preferable reducing agent, complex compound of borohydride is given, and sodium borohydride is more preferable.

The amount of the reducing agent used is different in the kind of the reducing agent, but for example, in the case of the complex compound of borohydride, it may be equal to or more than 0.25 times mole per mole of the compound of the general formula [13], and is preferably 0.25 to 2 times mole.

The reaction temperature is not particularly limited, but is from −20° C. to equal to or less than the boiling point of solvent, and is preferably 0 to 70° C.

The reaction time is not particularly limited, but is for 10 minutes to 50 hours, and is preferably for 30 minutes to 20 hours.

The compound of the general formula [5] obtained in this way may be used as it is in the next reaction without isolation, but it is preferable to isolate it by crystallizing the crystal.

The process of crystallization from aliphatic hydrocarbons such as hexane, cyclohexane and the like is preferable, the process of crystallization from hexane or cyclohexane is more preferable, and the process of crystallization from cyclohexane is further preferable.

Dehydration Reaction:

The compound of the general formula [6] can be produced by subjecting the compound of the general formula [5] to dehydration reaction in the presence of acid catalyst.

This reaction is usually carried out in the presence of solvent, the solvent used, if it does not affect an influence on the reaction, is not particularly limited, but for example, aliphatic hydrocarbons such as hexane, cyclohexane and the like;
aromatic hydrocarbons such as benzene, toluene, xylene and the like;
aliphatic halogenated hydrocarbons such as dichloromethane, chloroform, dichloroethane and the like;
ethers such as tetrahydrofuran, 1,2-dimethoxyethane, bis(2-methoxyethyl)ether, dioxane and the like;
amides such as N,N-dimethylformamide, N,N-dimethylacetamide, 1-methyl-2-pyrrolidone and the like;
sulfoxides such as dimethyl sulfoxide and the like;
esters such as methyl acetate, ethyl acetate and the like;
ketones such as acetone, 2-butanone and the like;
alcohols such as methanol, ethanol, propanol, 2-propanol, butanol and the like;
nitriles such as acetonitrile and the like;
aliphatic carboxylic acid such as acetic acid, propionic acid and the like;
and water and the like; are given, and these may be used in admixture.

As a preferable solvent, ketone is given, and acetone is more preferable.

The amount of the solvent used is not particularly limited, but is preferably 1 to 50 times volume per weight of the compound of the general formula [5], and is preferably 1 to 10 times (v/w).

As the acid catalyst used in this reaction, for example, Broensted acids such as hydrochloric acid, sulfuric acid, methanesulfonic acid, trifluoromethanesulfonic acid, p-toluenesulfonic acid, dichloroacetic acid and the like;
and Lewis acid such as aluminum chloride, boron trifluoride, boron trichloride and the like; are given, and p-toluenesulfonic acid is preferable.

The amount of the acid catalyst used may be equal to or more than 0.0001 times mole per mole of the compound of the general formula [5], and is 0.001 to 1 times mole.

The reaction temperature is not particularly limited, but is from −20° C. to equal to or less than the boiling point of solvent, and is preferably 0 to 70° C.

The reaction time is not particularly limited, but is for 10 minutes to 50 hours, and is preferably for 30 minutes to 20 hours.

[Production Process 2]

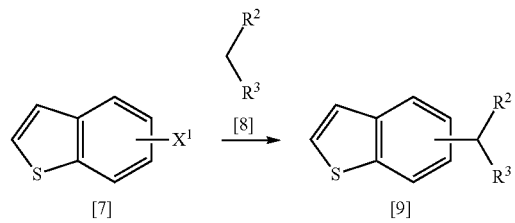

wherein $R^2$, $R^3$ and $X^1$ have the same meanings as the above.

As the compound of the general formula [8] or salts thereof, for example, diethyl malonate, di(tert-butyl)malonate, ethyl cyano acetate, tert-butyl cyano acetate, malononitrile and the like; are marketed.

The compound of the general formula [9] or salts thereof can be produced by subjecting the compound of the general formula [7] to coupling reaction with the compound of the general formula [8] or salts thereof in the presence of base and palladium catalyst, in the presence or absence of ligand, in the presence or absence of reducing agent.

This reaction is usually carried out in the presence of solvent, the solvent used, if it does not affect a bad influence on the reaction, is not particularly limited, but for example, aliphatic hydrocarbons such as hexane, cyclohexane and the like;

halogenated hydrocarbons such as dichloromethane, chloroform, dichloroethane and the like;

ethers such as tetrahydrofuran, 1,2-dimethoxyethane, bis(2-methoxyethyl)ether, dioxane and the like;

aromatic hydrocarbons such as benzene, toluene, xylene and the like;

amides such as N,N-dimethylformamide, N,N-dimethylacetamide, 1-methyl-2-pyrrolidone and the like;

sulfoxides such as dimethyl sulfoxide and the like;

esters such as ethyl acetate, butyl acetate and the like;

ketones such as acetone, 2-butanone and the like;

alcohols such as methanol, ethanol, propanol, butanol, 2-propanol, 2-methyl-2-propanol and the like;

and nitriles such as acetonitrile and the like; are given, and these may be used in admixture.

The amount of the solvent used is not particularly limited, but is preferably 1 to 20 times volume per weight of the compound of the general formula [7], and is preferably 1 to 10 times (v/w).

As the base used in this reaction, for example, metal alkoxide such as sodium methoxide, sodium ethoxide, potassium tert-butoxide and sodium tert-butoxide and the like;

inorganic base such as sodium hydroxide, potassium hydroxide, sodium carbonate, potassium carbonate, cesium carbonate, barium carbonate, sodium phosphate, potassium phosphate, sodium hydride and potassium hydride and the like;

organic base such as triethylamine, N,N-diisopropylethylamine, pyridine and the like; are given.

The amount of the base used may be equal to or more than 1 time mole per mole of the compound of the general formula [7], is preferably 2 to 10 times mole, and is more preferably 2 to 4 times mole.

As the palladium catalyst used in this reaction, for example, metal palladium such as palladium-carbon, palladium black and the like;

inorganic palladium salt such as palladium chloride;

organic palladium salt such as palladium acetate;

organopalladium complex such as tetrakis(triphenylphosphine)palladium (0), bis(triphenylphosphine)palladium (II) chloride, 1,1'-bis(diphenylphosphino)ferrocene palladium (II) chloride, tris(dibenzylideneacetone)dipalladium (0) and the like;

and polymer fixed organopalladium complex such as bis(acetate)triphenylphosphine palladium (II) carried in polymer, di(acetate)dicyclohexylphosphine palladium (II) carried in polymer and the like; are given.

The amount of the palladium catalyst used is not particularly limited, but is preferably 0.0001 to 1 times mole per mole of the compound of general formula [7], and is more preferably is 0.005 to 0.1 times mole.

As the ligand used, if desired, in this reaction, for example, trialkylphosphines such as trimethylphosphine, tri(tert-butyl) phosphine and the like;

tricycloalkylphosphines such as tricyclohexylphosphine and the like;

triarylphosphines such as triphenylphosphine, tritolylphosphine and the like;

trialkyl phosphites such as trimethyl phosphite, triethyl phosphite, tributyl phosphite and the like;

tricycloalkyl phosphites such as tricyclohexyl phosphite and the like;

triaryl phosphites such as triphenyl phosphite and the like;

imidazolium salt such as 1,3-bis(2,4,6-trimethylphenyl)imidazolium chloride and the like;

diketones such as acetylacetone, octafluoroacetylacetone and the like;

amines such as trimethylamine, triethylamine, tripropylamine, triisopropylamine and the like;

1,1'-bis(diphenylphosphino)ferrocene;

and 2,2-bis(diphenylphosphino)-1,1'-binaphthyl and the like; are given.

The amount of the ligand used is not particularly limited, but is preferably 0.0001 to 2 times mole per mole of the compound of general formula [7], and is more preferably 0.005 to 0.2 times mole.

As the reducing agent used, if desired, in this reaction, for example, complex compound of borohydride such as lithium borohydride, sodium borohydride, calcium borohydride, triacetoxy sodium borohydride, sodium cyano borohydride and the like; is given.

The amount of the reducing agent used is not particularly limited, but is preferably 0.0001 to 1 times mole per mole of the compound of general formula [7], and is more preferably 0.01 to 0.1 times mole.

The amount of the compound of general formula [8] is 1 to 5 times mole per mole of the compound of general formula [7], and is preferably 1 to 2 times mole.

This reaction may be carried out at 0 to 200° C., and preferably at 50 to 150° C. for 1 minute to 24 hours.

The compound of general formula [9] or salts thereof obtained in this way may be used as it is in the next reaction without isolation.

[Production Process 3]

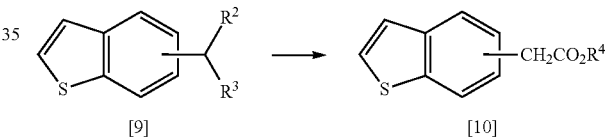

wherein $R^2$, $R^3$ and $R^4$ have the same meanings as the above.

The compound of the general formula [10] or salts thereof can be produced by reacting the compound of the general formula [9] or salts thereof with acid or base in the presence or absence of water, in the presence or absence of alcohol, subjecting it to decarboxylation reaction if necessary.

This reaction is usually carried out in the presence of solvent, the solvent used, if it does not affect a bad influence on the reaction, is not particularly limited, but for example, aliphatic hydrocarbons such as hexane, cyclohexane and the like;

halogenated hydrocarbons such as dichloromethane, chloroform, dichloroethane and the like;

ethers such as tetrahydrofuran, 1,2-dimethoxyethane, bis(2-methoxyethyl)ether, dioxane and the like;

aromatic hydrocarbons such as benzene, toluene, xylene and the like;

amides such as N,N-dimethylformamide, N,N-dimethylacetamide, 1-methyl-2-pyrrolidone and the like;

sulfoxides such as dimethyl sulfoxide and the like;

esters such as ethyl acetate, butyl acetate and the like;

ketones such as acetone, 2-butanone and the like;

alcohols such as methanol, ethanol, propanol, butanol, 2-propanol, 2-methyl-2-propanol and the like;

glycols such as ethylene glycol, propylene glycol, diethylene glycol and the like;

nitriles such as acetonitrile and the like;

and water and the like; are given, and these may be used in admixture.

The amount of the solvent used is not particularly limited, but is preferably 1 to 50 times volume per weight of the compound of the general formula [9] or salts thereof, and is more preferably 1 to 15 times (v/w).

As the acid used in this reaction, inorganic acid such as hydrochloric acid, sulfuric acid, phosphoric acid, hydrogen chloride, hydrogen bromide and the like;
organic carboxylic acid such as acetic acid, trichloroacetic acid, trifluoroacetic acid and the like;
and organic sulfonic acid such as methanesulfonic acid, p-toluenesulfonic acid and the like; are given.

The amount of the acid used may be equal to or more than 0.001 times mole per mole of the compound of the general formula [9] or salts thereof, and is preferably 0.01 to 5 times mole.

In addition, the acid may be used as solvent.

In addition, as the base used in this reaction, for example, metal alkoxide such as sodium methoxide, sodium ethoxide, potassium tert-butoxide and sodium tert-butoxide and the like;
inorganic base such as sodium hydroxide, potassium hydroxide, barium hydroxide, sodium carbonate, potassium carbonate and the like;
and organic base such as triethylamine, N,N-diisopropylethylamine, pyridine and the like; are given.

The amount of base used is 2 to 10 times mole per mole of the compound of general formula [9] or salts thereof, and is preferably 2 to 5 times mole.

The amount of water used, if desired, in this reaction, is not particularly limited, but is preferably 0.5 to 5 times volume per weight of the compound of general formula [9] or salts thereof in order to make it have the function of solvent.

As the alcohol used, if desired, in this reaction, for example, primary alcohols such as methanol, ethanol, propanol, butanol and the like; and glycols such as ethylene glycol, propylene glycol, diethylene glycol and the like; are given.

The amount of the alcohol used is not particularly limited, but is preferably 0.5 to 5 times volume per weight of the compound of general formula [9] or salts thereof in order to make it have the function of solvent.

This reaction may be carried out at 0 to 200° C., and preferably at 20 to 150° C. for 1 minute to 24 hours.

Decarboxylation reaction which may be performed if necessary is carried out by heating As the acid used, if desired, in this reaction, for example, inorganic acid such as hydrochloric acid, sulfuric acid, phosphoric acid, hydrogen chloride, hydrogen bromide and the like;
organic carboxylic acid such as acetic acid, trichloroacetic acid, trifluoroacetic acid and the like;
and organic sulfonic acid such as methanesulfonic acid, p-toluene sulfonic acid and the like; are given.

The amount of the acid used may be equal to or more than 0.001 times mole per mole of the compound of general formula [9] or salts thereof, and is preferably 0.01 to 5 times mole.

In addition, the acid may be used as solvent.

This reaction may be carried out if necessary in coexistent of solvent.

The solvent used, if it does not affect a bad influence on the reaction, is not particularly limited, but for example, aliphatic hydrocarbons such as hexane, cyclohexane and the like;
halogenated hydrocarbon such as dichloromethane, chloroform, dichloroethane and the like;
ethers such as tetrahydrofuran, 1,2-dimethoxyethane, bis(2-methoxyethyl)ether, dioxane and the like;
aromatic hydrocarbons such as benzene, toluene, xylene and the like;
amides such as N,N-dimethylformamide, N,N-dimethylacetamide, 1-methyl-2-pyrrolidone and the like;
sulfoxides such as dimethyl sulfoxide and the like;
esters such as ethyl acetate, butyl acetate and the like;
ketones such as acetone, 2-butanone and the like;
alcohols such as methanol, ethanol, propanol, butanol, 2-propanol, 2-methyl-2-propanol and the like;
glycols such as ethylene glycol, propylene glycol, diethylene glycol and the like;
nitriles such as acetonitrile and the like;
and water and the like; are given, and these may be used in admixture.

This reaction may be carried out at 50 to 200° C., and preferably at 50 to 150° C. for 1 minute to 24 hours.

[Production Process 4]

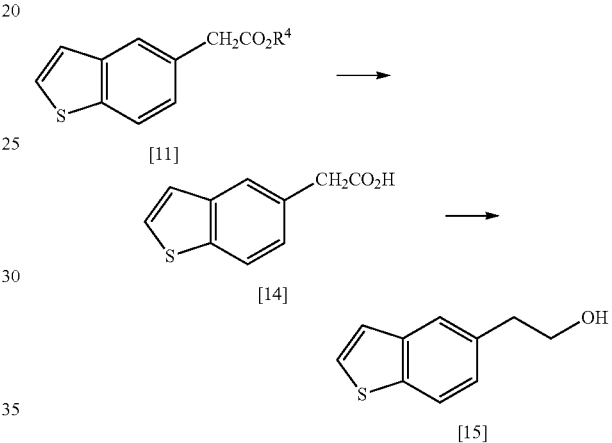

wherein R⁴ has the same meanings as the above.

2-(1-benzothiophen-5-yl)ethanol of the compound of the formula [15] can be produced by subjecting the compound of the general formula [11] or salts thereof to hydrolysis reaction if necessary, and deriving it to (1-benzothiophen-5-yl)acetic acid or salts thereof of the compound of the formula [14], subsequently subjecting (1-benzothiophen-5-yl)acetic acid or salts thereof to reduction reaction with an addition of activator in the presence of alkali metal borohydride.

This reaction is usually carried out in the presence of solvent, the solvent used, if it does not affect an influence on the reaction, is not particularly limited, but for example, ethers such as tetrahydrofuran, 1,2-dimethoxyethane, bis(2-methoxyethyl)ether, dioxane and the like; is given, and tetrahydrofuran is preferable.

In addition, these solvents may be mixed with a solvent of halogenated hydrocarbons such as dichloromethane, chloroform and the like;
aromatic hydrocarbons such as benzene, toluene, xylene and the like;
and aliphatic hydrocarbons such as hexane, cyclohexane, octane and the like; and the mixed solvent may be used.

The amount of the solvent used is not particularly limited, but is preferably 1 to 20 times volume per weight of the compound of the formula [14] or salts thereof, and is preferably 2 to 10 times (v/w).

As the alkali metal borohydride used in this reaction, for example, sodium borohydride, lithium borohydride, potassium borohydride and the like; are given, and sodium borohydride is preferable.

The amount of the alkali metal borohydride used may be equal to or more than 1 time mole per mole of the compound of the formula [14] or salts thereof, is preferably 1 to 10 times mole, and is more preferably 1 to 2 times mole.

As the activator used in this reaction, for example, protonic acid such as sulfuric acid, hydrogen chloride, trifluoroacetic acid and the like is given, and sulfuric acid and hydrogen chloride are preferable.

The amount of the activator used is different in the kind of the activator, but for example, but in the case of sulfuric acid it is preferably 0.5 to 1 times mole per mole of the alkali metal borohydride, and is more preferably 0.5 to 0.6 times mole.

In addition, the addition time of the activator is different in the kind of the activator, but in the case of sulfuric acid it is preferably for 10 minutes to 6 hours, and is more preferably for 30 minutes to 2 hours.

In addition, the activator may be dissolved in solvent appropriately, and the dissolved solvent may be added.

The reaction temperature is not particularly limited, but may be −20 to 150° C., and is preferably 0 to 80° C.

Further, the process by the addition of the activator at 0 to 30° C. and the subsequent reaction at 40 to 80° C. is more preferable, because generation of by-products can be suppressed.

In addition, the reaction time is not particularly limited, but is for 10 minutes to 50 hours, and is preferably for 1 to 20 hours.

In addition, the hydrolysis reaction of the compound of the general formula [11] or salts thereof which may be carried out if necessary may be performed by a reaction in a manner per se, for example, the compound of the formula [14] or salts thereof can be derived by subjecting it to hydrolysis reaction in the presence of base.

This reaction is usually carried out in the presence solvent, the solvent used, if it does not affect an influence on the reaction, is not particularly limited, but for example, aliphatic hydrocarbons such as hexane, cyclohexane and the like;
aromatic hydrocarbons such as benzene, toluene, xylene and the like;
halogenated hydrocarbons such as dichloromethane, chloroform and the like;
ethers such as tetrahydrofuran, 1,2-dimethoxyethane, bis(2-methoxyethyl)ether, dioxane and the like;
sulfoxides such as dimethyl sulfoxide and the like;
alcohols such as methanol, ethanol, propanol, butanol, 2-propanol, tert-butanol and the like;
and water and the like; are given, and these solvents may be used in admixture.

As a preferable solvent, a mixed solvent of aromatic hydrocarbons such as benzene, toluene and xylene and alcohols, and a mixed solvent of alcohols and water; are given, and a mixed solvent of toluene and methanol and a mixed solvent of methanol and water are preferable.

The amount of the solvent used is not particularly limited, but is preferably 0.5 to 10 times volume per weight of the compound of the general formula [11] or salts thereof, and is more preferably 0.5 to 5 times (v/w).

As the base used in this reaction, for example, metal alkoxide such as sodium methoxide, sodium ethoxide, potassium tert-butoxide, sodium tert-butoxide and the like;
and inorganic base such as sodium hydroxide, potassium hydroxide, barium hydroxide, sodium carbonate, potassium carbonate and the like; are given.

As a preferable base, inorganic base is given, and sodium hydroxide and potassium hydroxide are preferable.

The amount of base used may be equal to or more than 1 time mole per mole of the compound of the general formula [11] or salts thereof, and is preferably 1 to 3 times mole.

This reaction is preferably performed by an addition of water.

The amount of water added may be equal to or more than 1 time mole per mole of the compound of the general formula [11] or salts thereof, is preferably 0.1 to 10 times (v/w), and is more preferably 0.3 to 2 times (v/w) in order to make it have the function of solvent.

The reaction temperature is not particularly limited, but it may be from 0° C. to equal to or less than the boiling point of solvent, and is preferably 10 to 40° C.

The reaction time is not particularly limited, but may be for 10 minutes to 50 hours, and is preferably for 1 to 24 hours.

The compound of the formula [14] or salts thereof obtained in this way can be isolated from the reaction mixture after the termination of the reaction in the usual manner.

For example, after the termination of the reaction, it can be isolated by acidification with a diluted hydrochloric acid, extraction with organic solvent such as toluene, and subsequent removal of solvent.

In addition, it can be isolated as a salt by the way of an addition of base into the extract.

As the salt of the compound of the formula [14], the salt, if it is usually known for a salt in acidic group such as carboxyl group, is not particularly limited, but for examples, salts with alkali metal such as sodium, potassium, cesium and the like; salts with alkali earth metal such as calcium, magnesium and the like;
ammonium salts,
and salts with nitrogen containing organic base such as trimethyl amine, triethylamine, tributylamine, N,N-diisopropylethylamine, pyridine, N-methylpiperidine, N-methylmorpholine, diethylamine, dicyclohexylamine and the like; are given.

As a preferable salt, a salt with alkali metal such as sodium and potassium is given, and a sodium salt is preferable.

[Production Process 5]

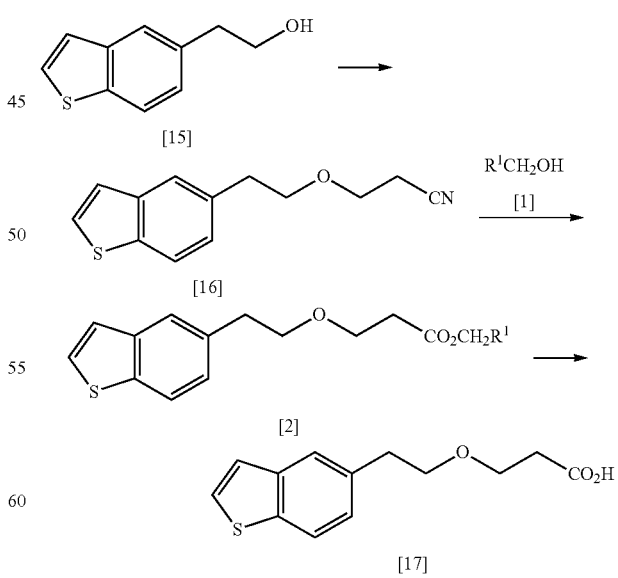

wherein R[1] has the same meanings as the above.

3-(2-(1-benzothiophen-5-yl)ethoxy)propionic acid of the compound of the formula [17] or salts thereof can be produced by subjecting the compound of the formula [15] to Michael addition reaction with acrylonitrile in the presence of base to obtain the compound of the formula [16], subsequently subjecting the compound of the formula [16] to reaction with the alcohol of the general formula [1] in the presence of acid, subsequently deriving it to the compound of general formula [2], and subjecting the compound of general formula [2] to hydrolysis reaction in the presence of base.

The present process for production is explained below in detail.

Michael Addition Reaction:

The compound of the formula [16] can be produced by subjecting the compound of the formula [15] to Michael addition reaction with acrylonitrile in the presence of base.

This reaction is usually carried out in the presence of solvent, the solvent used, if it does not affect an influence on the reaction, is not particularly limited, but for example, aliphatic hydrocarbons such as hexane, cyclohexane and the like;
aromatic hydrocarbons such as benzene, toluene, xylene and the like;
halogenated hydrocarbons such as dichloromethane, chloroform and the like;
ethers such as tetrahydrofuran, 1,2-dimethoxyethane, bis(2-methoxyethyl)ether, dioxane and the like;
sulfoxides such as dimethyl sulfoxide and the like;
and tertiary alcohols such as tert-butanol, tert-amyl alcohol and the like; are given, and these may be used in admixture.

As a preferable solvent, a sole solvent of aromatic hydrocarbons and a mixed solvent of aromatic hydrocarbons, ethers and tertiary alcohols are given, a sole solvent of aromatic hydrocarbons, a mixed solvent of aromatic hydrocarbons and ethers, and a mixed solvent of aromatic hydrocarbons and tertiary alcohols are preferable, toluene, a mixed solvent of toluene and tetrahydrofuran, a mixed solvent of toluene and tert-butanol, and a mixed solvent of toluene and tert-amyl alcohol are more preferable.

The amount of the solvent used is not particularly limited, but is preferably 0.5 to 10 times volume per weight of the compound of the formula [15], and is more preferably 0.5 to 3 times (v/w).

In addition, as an additive to these solvents, primary alcohols such as small amount of methanol and ethanol and the like;
secondary alcohols such as 2-propanol and the like;
and water and the like; these may be mixed.

The amount of the additive used is equal to or less than 0.5 times volume per weight of the compound of the formula [15], and is preferably equal to or less than 0.1 times (v/w).

As the base used in this reaction, for example, organic base such as 1,8-diazabicyclo[5.4.0]undec-7-ene (DBU), tetramethylammonium hydroxide, benzyltrimethylammonium hydroxide and the like;
metal alkoxide such as sodium methoxide, sodium ethoxide, potassium tert-butoxide, sodium tert-butoxide and the like;
inorganic base such as sodium hydroxide, potassium hydroxide, sodium hydride and the like; are given.

As a preferable base, organic base and metal alkoxide are given, benzyltrimethylammonium hydroxide and potassium tert-butoxide are more preferable.

The amount of the base used may be equal to or more than 0.0001 times mole per mole of the compound of the formula [15], and is preferably 0.01 to 0.1 times mole.

In addition, this reaction may be carried out in the presence of catalyst.

As the catalyst used, if desired, quaternary ammonium salt which is usually known is given, tetrabutylammonium bromide, benzyltrimethylammonium chloride and benzyltrimethylammonium bromide are preferable.

The amount of the catalyst used may be equal to or more than 0.0001 times mole per mole of the compound of the formula [15], and is preferably 0.01 to 0.1 times mole.

As the base, for example, in the case that inorganic base such as sodium hydroxide and potassium hydroxide and the like are used, it is preferable to perform this reaction in the presence of catalyst.

The amount of acrylonitrile used in this reaction may be equal to or more than 1 time mole per mole of the compound of the formula [15], and is preferably 1 to 2 times mole.

The reaction temperature is not particularly limited, but may be from 0° C. to equal to or less than the boiling point of solvent, and is preferably 0 to 35° C.

The reaction time is not particularly limited, but may be for 1 minute to 24 hours, and is preferably for 30 minutes to 4 hours.

The compound of the formula [16] obtained in this way may be used as it is in the next reaction without isolation.

Esterification Reaction:

The compound of the general formula [2] can be produced by subjecting the compound of formula [16] to reaction with the alcohol of the general formula [1] in the presence acid.

As the acid used in this reaction, for example, inorganic acid such as hydrochloric acid, sulfuric acid, hydrogen chloride, hydrogen bromide and the like;
and organic sulfonic acid such as methanesulfonic acid, p-toluenesulfonic acid and the like; are given.

As a preferable acid, inorganic acid is given, and sulfuric acid and hydrogen chloride are more preferable.

The amount of the acid used is different in the amount of the solvent used, but may be equal to or more than 1 time mole per mole of the compound of the formula [16], and is preferably 2 to 10 times mole.

As the alcohol of general formula [1] used in this reaction, a straight chain alkyl alcohols such as methanol, ethanol, propanol, butanol, pentanol and the like;
branched chain alkyl alcohols such as isobutanol and the like;
substituted alkyl alcohols such as methoxy ethanol, chloroethanol, cyclohexanethanol and the like;
and aralkyl alcohols such as benzyl alcohol, phenethyl alcohol and the like; are given.

As a preferable alcohol, straight chain alkyl alcohols are given, and methanol, ethanol, propanol and butanol are more preferable.

The amount of the alcohol used may be equal to or more than 1 time mole pre mole of the compound of the formula [16], is preferable 0.5 to 10 times (v/w), and is more preferably 0.5 to 5 times (v/w) in order to make it have the function of solvent.

In this reaction, in the case that inorganic acid such as sulfuric acid and hydrogen chloride and the like;
and organic sulfonic acid such as methanesulfonic acid and the like; are used, it is preferable to perform the reaction with an addition of water.

The amount of water added may be equal to or more than 1 time mole per mole of the compound of the formula [16], is preferably 1 to 10 times mole, and is more preferably 1 to 6 times mole.

This reaction may be performed in the presence of solvent.

As the solvent used, it is not particularly limited, but the same as Michael addition reaction is given.

The reaction temperature is not particularly limited, but may be from 0° C. to equal to or less than the boiling point of solvent, and is preferably 20 to 150° C.

The reaction time is not particularly limited, but may be for 10 minutes to 50 hours, and is preferably for 1 to 24 hours.

The compound of the general formula [2] obtained in this way may be used as it is to the next reaction without isolation.

Hydrolysis Reaction:

The compound of the general formula [17] or salts thereof can be produced by hydrolyzing the compound of formula [2] in the presence of base.

This reaction is usually carried out in the presence of solvent, the solvent used, if it does not affect an influence on the reaction, is not particularly limited, but for example, aliphatic hydrocarbons such as hexane, cyclohexane and the like; aromatic hydrocarbons such as benzene, toluene, xylene and the like;

halogenated hydrocarbons such as dichloromethane, chloroform and the like;

ethers such as tetrahydrofuran, 1,2-dimethoxyethane, dioxane and the like;

sulfoxides such as dimethyl sulfoxide and the like;

alcohols such as methanol, ethanol, propanol, butanol, 2-propanol, tert-butanol and the like;

and water and the like; are given, and these solvents may be used in admixture.

As a preferable solvent, a mixed solvent of the solvent used in the esterification reaction and alcohols, and a mixed solvent of alcohols water are given, and a mixed solvent of toluene and methanol, and a mixed solvent of methanol and water are more preferable.

The amount of the solvent used is not particularly limited, but is preferably 0.5 to 10 times volume per weight of the compound of the general formula [2], and is more preferably 0.5 to 3 times (v/w).

The reaction temperature is not particularly limited, but may be from 0° C. to equal to or less than the boiling point of solvent, and is preferably 10 to 40° C.

The reaction time is not particularly limited, but may be for 10 minutes to 50 hours, and is preferably 1 to 24 hours.

The compound of the formula [17] or salts thereof obtained in this way can be isolated from the reaction mixture after the termination of the reaction in the usual manner.

For example, after the termination of the reaction, it can be isolated by acidification with diluted hydrochloric acid, subsequent extraction with organic solvent such as toluene and removal of solvent.

In addition, it can be isolated as a salt by an addition of base into the extract.

As the salt of the compound of the formula [17], the salt, if it is usually known for a salt in acidic group such as carboxyl group, is not particularly limited, but for example, salts with alkali metal such as sodium, potassium, cesium and the like;

salts with alkali earth metal such as calcium, magnesium and the like;

ammonium salt, and salts with nitrogen containing organic base such as trimethyl amine, triethylamine, tributylamine, N,N-diisopropylethylamine, pyridine, N-methylpiperidine, N-methylmorpholine, diethylamine, dicyclohexylamine and the like; are given.

As a preferable salt, a salt with alkali metal such as sodium and potassium and the like is given, and a sodium salt is more preferable.

[Production Processes 6]

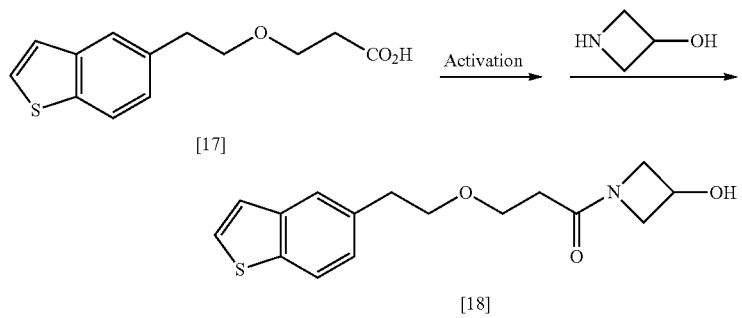

As the base used in this reaction, for example, metal alkoxide such as sodium methoxide, sodium ethoxide, potassium tert-butoxide, sodium tert-butoxide and the like;

and inorganic base such as sodium hydroxide, potassium hydroxide, barium hydroxide, sodium carbonate, potassium carbonate and the like; are given.

As a preferable base, inorganic base is given, and sodium hydroxide and potassium hydroxide are preferable.

The amount of the base used may be equal to or more than 1 time mole per mole of the compound of the general formula [2], and is preferably 1 to 3 times mole.

This reaction is preferably performed with an addition of water.

The amount of water added may be equal to or more than 1 time mole per mole of the compound of the general formula [2], is preferably 0.1 to 10 times (v/w), and is more preferably 0.3 to 2 times (v/w) in order to make it have the function of solvent.

1-(3-(2-(1-benzothiophen-5-yl)ethoxy)propionyl)azetidin-3-ol of the compound of the formula [18] can be produced by deriving the compound of the formula [17] or salts thereof to a reactive derivative, subsequently subjecting the reactive derivative to amidation reaction with 3-azetidinol or salts thereof in the presence of base.

The present process for production is explained below in detail.

Derivation to Reactive Derivative:

The compound of formula [17] or salts thereof can be derived to a reactive derivative by reacting it with an activator.

As the reactive derivative, for example, an acid halide, an acid anhydride, an activated amide and an activated ester and the like; are given, and an acid halide is preferable.

As the process of deriving it to the reactive derivative, for example, the derivation to the acid halide with the use of a halogenating agent such as thionyl chloride, oxalyl chloride, phosphorus trichloride, phosphorous pentachloride and the like;

the derivation to the acid anhydride by condensation with an acid halide such as ethyl chloroformate, isobutyl chloroformate, pivaloyl chloride and the like;
the derivation to the activated amide by use of imidazole condensation and an activated amidation agent such as carbonyldiimidazole and the like;
and the derivation to the activated ester by condensation with p-nitrophenol, 2-mercaptobenzothiazole and the like; are given.

As the derivation to the reactive derivative, the derivation to the acid halide by use of a halogenating agent is preferable, and the derivation to the acid chloride by use of thionyl chloride is more preferable.

The amount of the activator used in this derivation is different in the kind of the activator, but for example, in the case of thionyl chloride, it may be equal to or more than 0.5 times mole per mole of the compound of the formula [17] or salts thereof, and is preferably 1 to 2 times mole.

This reaction is usually carried out in the presence of solvent, the solvent used, if it does not affect an influence on the reaction, is not particularly limited, but for example, aliphatic hydrocarbons such as hexane, cyclohexane and the like;
aromatic hydrocarbons such as benzene, toluene, xylene and the like;
halogenated hydrocarbons such as dichloromethane, chloroform and the like;
ethers such as tetrahydrofuran, 1,2-dimethoxyethane, bis(2-methoxyethyl)ether, dioxane and the like;
amides such as N,N-dimethylformamide, N,N-dimethylacetamide, 1-methyl-2-pyrrolidone and the like;
sulfoxides such as dimethyl sulfoxide and the like;
esters such as methyl acetate, ethyl acetate and the like;
ketones such as acetone, 2-butanone and the like;
and nitriles such as acetonitrile and the like; are given, and these may be used in admixture.

As a preferable solvent, aromatic hydrocarbons such as benzene, toluene and xylene and the like and ethers such as tetrahydrofuran, 1,2-dimethoxyethane, bis(2-methoxyethyl)ether, dioxane and the like are given, and toluene and 1,2-dimethoxyethane are preferable.

The amount of the solvent used is not particularly limited, but is preferably 1 to 20 times volume per weight of the compound of the formula [17] or salts thereof, and is more preferably 1 to 10 times (v/w).

The reaction temperature is not particularly limited, but is preferably −60 to 150° C., and is more preferably −30 to 120° C.

The reaction time is not particularly limited, but is for 10 minutes to 50 hours, and is preferably 30 minutes to 20 hours.

The reactive derivative of the compound of the formula [17] or salts thereof derived in this way can be isolated and purified, but it is preferable to proceed to the next reaction without isolation.

Amidation Reaction:

The compound of the formula [18] can be produced by reacting the solution of the reactive derivative of the compound of the formula [17] or salts thereof described above with 3-azetidinol or salts thereof in the presence of base.

As the base used in this reaction, for example, organic base such as triethylamine, diisopropylethylamine, 1,8-diazabicyclo[5.4.0]undec-7-ene (DBU), pyridine and the like;
and inorganic base such as sodium hydroxide, potassium hydroxide, sodium carbonate, potassium carbonate, sodium hydrogen carbonate, potassium hydrogencarbonate and the like; are given.

As a preferable base, inorganic base is given, and sodium hydroxide is more preferably.

The amount of the base used may be equal to or more than 1 time mole per mole of the compound of the formula [17] or salts thereof, and is preferably 1 to 10 times mole.

The amount of 3-azetidinol or salts thereof may be equal to or more than 1 time mole per mole of the compound of the formula [17] or salts thereof, and is preferably 1 to 2 times mole.

In addition, it is preferable to use 3-azetidinol or salts thereof in aqueous solution.

The amount of water having 3-azetidinol or salts thereof dissolved is not particularly limited, but is preferably 1 to 20 times volume per weight of the compound of the formula [17] or salts thereof, and is preferably 1 to 10 times (v/w).

The reaction temperature is not particularly limited, but is preferably −60 to 100° C., and is more preferably −30 to 50° C.

The reaction time is not particularly limited, but is for 10 minutes to 50 hours, and is preferably for 30 minutes to 20 hours.

After the termination of the reaction, the compound of the formula [18] obtained in this way can be isolated and purified by crystallization from the reaction mixture by performing treatments such as neutralization of the reaction mixture and dilution with water if necessary, and subsequent operation of warming and cooling.

[Production Process 7]

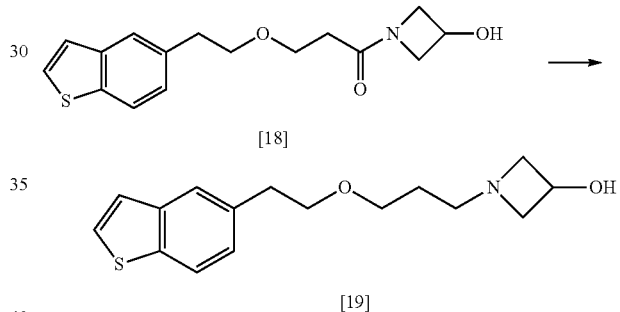

1-(3-(2-(1-benzothiophen-5-yl)ethoxy)propyl)azetidin-3-ol of the compound of the formula [19] or salts thereof can be produced by subjecting the compound of the formula [18] to reduction reaction with an addition of activator such as a protonic acid, a methylating agent and a silylating agent and the like in the presence of alkali metal borohydride.

This reaction is usually carried out in the presence of solvent, the solvent used, if it does not affect an influence on the reaction, is not particularly limited, but for example, ethers such as tetrahydrofuran, 1,2-dimethoxyethane, bis(2-methoxyethyl)ether, dioxane and the like; is given, and tetrahydrofuran is more preferable.

In addition, these solvents may be used in admixture of halogenated hydrocarbons such as dichloromethane, chloroform and the like;
aromatic hydrocarbons such as benzene, toluene, xylene and the like;
and aliphatic hydrocarbons such as hexane, cyclohexane, octane and the like.

The amount of the solvent used is preferably 1 to 20 times volume per weight of the compound of the formula [18], and is more preferably 3 to 10 times (v/w).

As the alkali metal borohydride used in this reaction, for example, sodium borohydride, lithium borohydride, potassium borohydride and the like; are given, and sodium borohydride is preferable.

The amount of the alkali metal borohydride is preferably 1 to 10 times mole per mole of the compound of the formula [18], and is more preferably 2 to 3 times mole.

As the activator used in this reaction, for example, protonic acid such as sulfuric acid, hydrogen chloride, trifluoroacetic acid and the like;
methylating agent such as dimethyl sulfate and the like;
and silylating agent such as trimethylsilyl chloride and the like; are given.

As a preferable activator, protonic acid such as sulfuric acid, hydrogen chloride and the like; is given, and sulfuric acid is more preferable.

The amount of the activator used is different in the kind of the activator, but for example, in the case of sulfuric acid, it is preferably 0.5 to 1 times mole per mole of alkali metal borohydride, and is more preferably 0.5 to 0.6 times mole.

In addition, the addition time of the activator is different in the kind of the activator, but in the case of sulfuric acid, it is preferably for 10 minutes to 6 hours, and is more preferably for 30 minutes to 4 hours.

In addition, the activator may be dissolved in solvent appropriately, and the dissolved solvent may be added.

Further, in the case that the amount of the alkali metal borohydride is 2.0 to 2.2 times mole per mole of the compound of the formula [18] and the amount of sulfuric acid is 0.5 to 0.6 times mole per mole of the alkali metal borohydride and the dropping time of the sulfuric acid is 1 to 4 hours, the compound of the formula [19] or salts thereof having high purity can be obtained because of the further suppression of the formation of by-products The reaction temperature is not particularly limited, but may be −20 to 150° C., and is preferably 0 to 70° C.

After an addition of activator at 0 to 30° C., it is preferable to react at 30 to 70° C., and after an addition of activator at 0 to 30° C., it is more preferable to react at 40 to 60° C.

The reaction time is not particularly limited, but may be for 10 minutes to 50 hours, is preferably for 1 to 20 hours.

In the present invention, as a preferable process for production, the following process is given, the process by suspending the compound of the formula [18] in ether (3-10 times (v/w)), adding alkali metal borohydride (2 to 3 times mole), adding activator at 0 to 30° C., and subsequently reacting at 30 to 70° C. for 1 to 20 hours is preferable, the process by suspending the compound of the formula [18] in ether (3 to 10 times (v/w)), adding sodium borohydride (2 to 3 times mole), adding protonic acid (0.5 to 1 times mole per mole of sodium borohydride) at 0 to 30° C., and subsequently reacting at 30 to 70° C. for 1 to 20 hours is more preferable, and the process by suspending the compound of formula [18] in tetrahydrofuran (3 to 10 times (v/w)), adding sodium borohydride (2.0 to 2.2 times mole), adding sulfuric acid (0.5 to 0.6 times mole per mole of sodium borohydride) at 0 to 30° C. for 1 to 4 hours, and subsequently reacting at 40 to 60° C. for 1 to 20 hours is further preferable.

After the termination of the reaction, the compound of the formula [19] or salts thereof obtained in this way can be isolate in usual manner.

For example, after the termination of the reaction, it can be isolated by adding 6.0 mol/L hydrochloric acid to decompose an excessive reducing agent, cooling to room temperature, subsequently making the reaction mixture alkaline with aqueous sodium hydroxide, extracting with organic solvent such as ethyl acetate, and subsequently removing the solvent from the extract.

In addition, it can be isolated as a salt by an addition of acid into the extract.

As the salt of the compound of the formula [19], the salt, if it is usually known for a salt in basic group such as amino group, is not particularly limited, but for example, salts with mineral acid such as hydrochloric acid, hydrobromic acid, nitric acid, sulfuric acid and the like;
salts with organic carboxylic acid such as formic acid, acetic acid, citric acid, oxalic acid, fumaric acid, maleic acid, succinic acid, malic acid, tartaric acid, aspartic acid, trichloroacetic acid, trifluoroacetic acid and the like;
and salts with sulfonic acid such as methanesulfonic acid, benzenesulfonic acid, toluenesulfonic acid, mesitylene sulfonic acid, naphthalenesulfonic acid and the like; are given.

As a preferable salt, a pharmacologically acceptable salt is given, and a salt with maleic acid is more preferable.

In the compound of the present invention, if isomer (for example, optical isomer), hydrate, solvate and various kinds of crystalline forms exist, the present invention includes these all.

In addition, in the compound used by the process for production described above, if isomer (for example, optical isomer), hydrate, solvate and various kinds of crystal form exist, all these can be used in the process for production of the present invention.

EXAMPLES

Next, the present invention will be described in the following reference examples and examples. However, the present invention is not intended to be limited thereto.

The mixing ratios in the eluents are by volume. A case without description in particular, the carrier in silica gel column chromatography is B.W. silica gel, BW-127ZH or PSQ100B (product of Fuji Silysia Chemical Ltd.).

The abbreviations in examples mean the following: Me: methyl, Et: ethyl, Pr: propyl, Bu: butyl, $^t$Bu: tert-butyl DMSO-$d_6$: dimethylsulfoxide-$d_6$ Reference Example 1

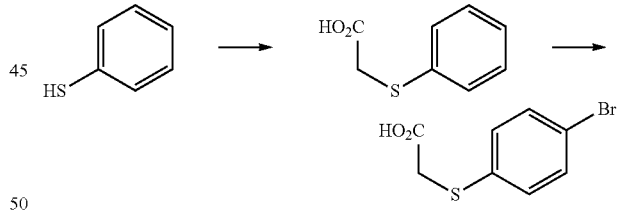

To water (275 mL) suspension of 546 g of thiophenol was dropwise added water (550 mL) solution of 585 g of potassium hydroxide at no more than 20° C. Next, thereto was dropwise added a water (825 mL) solution of 492 g of chloroacetic acid, which was then stirred at 80 to 90° C. for 3 hours. After cooling the reaction mixture, the pH was adjusted to 1.5 with hydrochloric acid, and thereto were added 1650 mL of dichloromethane and 550 mL of water. The organic layer was separated, and anhydrous magnesium sulfate was added. Insoluble matter was filtered off, and to the filtrate was added 5.95 g of iron(III) chloride, and dropwise added 832 g of Bromine at 5 to 10° C., which was then stirred at room temperature for 5 hours. After cooling the reaction solution to 5° C., thereto was dropwise added water (825 mL) solution of 187 g of sodium sulfite, and the pH was adjusted 1.2 with hydrochloric acid. After stirring at 5 to 10° C. for 1 hour, the precipitate was collected by filtration to provide solid matter. To this solid matter was added 2000 mL of toluene, from which water was removed by heating and azeotropic distillation. The reaction mixture was cooled to 5° C. over a period of 2 hours. After stirring at the same temperature for 1 hour, crystals precipitate was collected by filtration to provide 1108 g of (4-bromophenylthio)acetic acid as white solid form.

¹H-NMR(CDCl₃) δ value: 3.65 (2H, s), 7.25-7.35 (2H, m), 7.40-7.50 (1H, m).

Reference Example 2

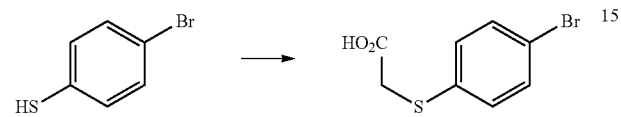

To water (600 mL) solution of 88.9 g of sodium hydroxide was added 200 g of 4-bromothiophenol and dropwise added water (300 mL) solution of 105 g of chloroacetic acid, which was then stirred at 60 to 70° C. for 1 hour. After cooling the reaction mixture to 40° C., thereto were added 140 mL of hydrochloric acid and 600 mL of toluene, which was then heated to 80° C. The organic layer was separated and slowly cooled to 5° C. After stirring at the same temperature for 1 hour, the crystals precipitate was collected by filtration to provide 243 g of (4-bromophenylthio)acetic acid as white solid form.

The Chemical shift values of ¹H-NMR spectral in CDCl₃ agreed with the values of reference example 1.

Example 1-1

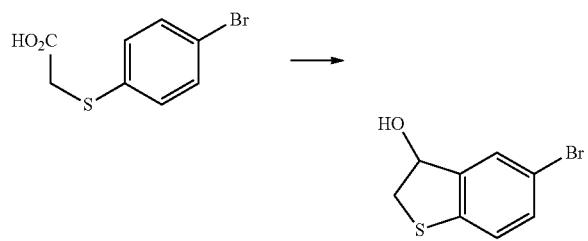

To dichloromethane (750 mL) suspension of 250 g of (4-bromophenylthio)acetic acid were added 2.5 mL of N,N-dimethylformamide and 132 g of thionyl chloride, which was then refluxed for 1 hour. After cooling the reaction mixture to 20° C., thereto was dropwise added dichloromethane (1500 mL) suspension of 148 g of aluminum chloride at 5 to 15° C., which was then stirred at 15 to 25° C. for 1.5 hours. Next, this reaction mixture was added dropwise to a mixed solution of 1310 mL of water and 188 mL of hydrochloric acid under cooling. The organic layer was separated, thereto was added 1250 mL of water, and the pH was adjusted to 3.0 with 5% potassium carbonate aqueous solution. The organic layer was separated and cooled to 5° C. Thereto were added 15.3 g of sodium borohydride and 500 mL of methanol, which was then stirred at 10 to 20° C. for 2 hours. To the reaction solution was added 750 mL of water, followed by adjustment to pH7.0 using acetic acid and left unattended in room temperature overnight. To the reaction solution was added 200 mL of 5% potassium hydroxide aqueous solution, and the organic layer was separated. To the organic layer was 25.0 g of activated carbon, which was then stirred at room temperature. Insoluble matter was filtered off, and the solvent of filtrate was distilled off. To the resultant residue was added cyclohexane, the crystals precipitated were collected by filtration to provide 194 g of 5-bromo-2,3-dihydro-1-benzothiophen-3-ol as pale red solid form.

¹H-NMR(CDCl₃) δ value:
2.18 (1H, d, J=8.3 Hz), 3.30 (1H, dd, J=12.0, 4.4 Hz), 3.61 (1H, dd, J=12.0, 6.3 Hz), 5.30-5.40 (1H, m), 7.11 (1H, d, J=8.3 Hz), 7.35 (1H, dd, J=8.3, 2.0 Hz), 7.50 (1H, d, J=2.0 Hz).

Example 1-2

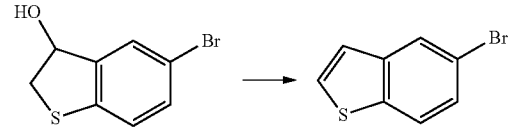

To acetone (600 mL) solution of 300 g of 5-bromo-2,3-dihydro-1-benzothiophen-3-ol was added 12.4 g of p-toluenesulfonic acid monohydrate, which was then refluxed for 2 hours. To the reaction solution was added 15.0 g of activated carbon, which was then stirred. Insoluble matter was filtered off and washed with 300 mL of acetone. The filtrate and washings were combined, to which was dropwise added 2700 mL of water at 5 to 15° C. The precipitate was collected by filtration to provide 268 g of 5-bromo-1-benzothiophene as pale purple solid form.

¹H-NMR(CDCl₃) δ value:
7.27 (1H, d, J=5.4 Hz), 7.44 (1H, dd, J=8.5, 1.9 Hz), 7.48 (1H, d, J=5.4 Hz), 7.74 (1H, d, J=8.5 Hz), 7.97 (1H, d, J=1.9 Hz).

Example 2-1

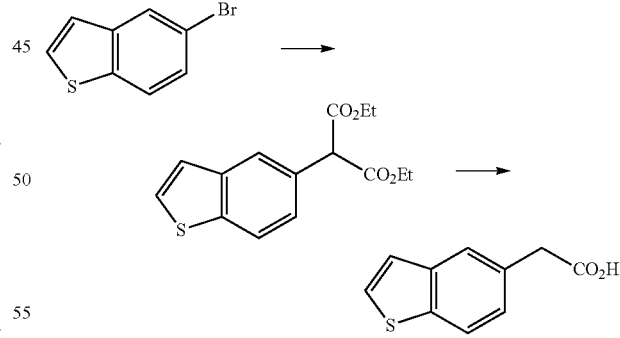

(1) To 1,2-dimethoxyethane (10 mL) suspension of 0.02 g of tris(dibenzylideneacetone)dipalladium(0) were added 0.11 g of 10% (w/w) tri(tert-butyl)phosphine/hexane, 1.76 g of cesium carbonate, 0.50 g of 5-bromobenzothiophene and 0.45 g of diethyl malonate, which was then refluxed for 2 hours. To the reaction mixture were added water and ethyl acetate, followed by adjustment to pH2 using 2 mol/L hydrochloric acid. The organic layer was separated, and dried over anhydrous magnesium sulfate, followed by distilling off the solvent under reduced pressure. The resultant residue was purified using silica gel column chromatography (eluent; hexane:ethyl acetate=10:1) to provide 0.69 g of diethyl 2-(1-benzothiophen-5-yl)malonate as white solid form.

$^1$H-NMR(CDCl$_3$) δ value:
1.27 (6H, t, J=7.1 Hz), 4.1-4.3 (4H, m), 4.73 (1H, s), 7.33 (1H, d, J=5.4 Hz), 7.40 (1H, dd, J=8.3, 2.0 Hz), 7.45 (1H, d, J=5.4 Hz), 7.87 (1H, d, J=8.3 Hz), 7.87 (1H, d, J=2.0 Hz).

(2) To ethylene glycol (1.0 mL) suspension of 0.25 g of diethyl 2-(1-benzothiophen-5-yl)malonate were added 1.0 mL of 40% (w/w) potassium hydroxide aqueous solution and 0.3 mL of water, which was then refluxed for 2 hours. To the reaction mixture were added water and toluene, and the aqueous layer was separated. The pH was adjusted to 2 with 6 mol/L hydrochloric acid, and thereto was added ethyl acetate. The organic layer was separated, and dried over anhydrous magnesium sulfate, followed by distilling off the solvent under reduced pressure. The resultant residue was suspended to 5 mL of xylene, and thereto was added 0.01 g of p-toluenesulfonic acid monohydrate, which was then refluxed for 30 minutes. The solvent was distilled off under reduced pressure, and to the resultant residue were added toluene and cyclohexane. The precipitate was collected by filtration to provide 0.02 g of 2-(1-benzothiophen-5-yl)acetic acid as pale yellow solid form.

$^1$H-NMR(CDCl$_3$) δ value:
3.76 (2H, s), 7.2-7.3 (1H, m), 7.29 (1H, d, J=5.4 Hz), 7.44 (1H, d, J=5.4 Hz), 7.73 (1H, s), 7.83 (1H, d, J=8.1 Hz).

Example 2-2

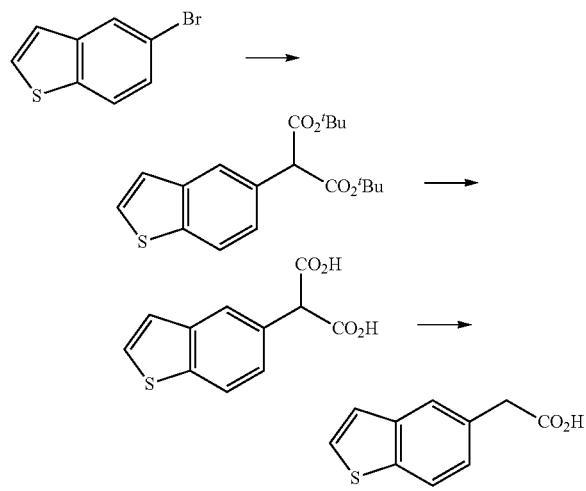

(1) To 1,2-dimethoxyethane (10 mL) solution of 0.11 g of 10% (w/w) tri(tert-butyl)phosphine/hexane were added 0.02 g of tris(dibenzylideneacetone)dipalladium(0), 1.76 g of cesium carbonate, 0.50 g of 5-bromobenzothiophene and 0.61 g of tert-butyl malonate, which was then refluxed for 2 hours. Next, thereto were added 0.02 g of tris(dibenzylideneacetone)dipalladium(0) and 0.11 g of 10% (w/w) tri(tert-butyl)phosphine/hexane, which was then refluxed for 1 hour. This reaction mixture was added to a mixed solution of 30 mL of water and 20 mL of ethyl acetate, and the pH was adjusted to 3 with 6 mol/L hydrochloric acid. The organic layer was separated, and dried over anhydrous magnesium sulfate, followed by distilling off the solvent under reduced pressure. The resultant residue was purified using silica gel column chromatography (eluent; hexane:ethyl acetate=20:1) to provide 0.49 g of di(tert-butyl) 2-(1-benzothiophen-5-yl)malonate as white solid form.

$^1$H-NMR(CDCl$_3$) δ value:
1.47 (18H, s), 4.55 (1H, s), 7.32 (1H, d, J=5.4 Hz), 7.39 (1H, dd, J=8.5, 1.7 Hz), 7.43 (1H, d, J=5.4 Hz), 7.84 (1H, d, J=1.7 Hz), 7.86 (1H, d, J=8.5 Hz).

(2) To toluene (2.5 mL) solution of 0.25 g of di(tert-butyl) 2-(1-benzothiophen-5-yl)malonate was added 0.01 g of p-toluenesulfonic acid monohydrate, which was then refluxed for 1 hour. After cooling the reaction mixture, the precipitate was collected by filtration to provide 0.14 g of 2-(1-benzothiophen-5-yl)malonic acid as white solid form.

$^1$H-NMR(CDCl$_3$) δ value:
4.80 (1H, s), 7.3-7.5 (1H, m), 7.47 (1H, d, J=5.5 Hz), 7.77 (1H, d, J=5.5 Hz), 7.89 (1H, s), 7.97 (1H, d, J=8.3 Hz).

(3) To xylene (2 mL) suspension of 0.10 g of 2-(1-benzothiophen-5-yl)malonic acid was added 4 mg of p-toluenesulfonic acid monohydrate, which was then refluxed for 1 hour. The solvent was distilled off under reduced pressure, and to the resultant residue was added cyclohexane. The precipitate was collected by filtration to provide 0.08 g of 2-(1-benzothiophen-5-yl)acetic acid as white solid form.

The Chemical shift values of $^1$H-NMR spectral in CDCl$_3$ agreed with the values of example 2-1 (2).

Example 2-3

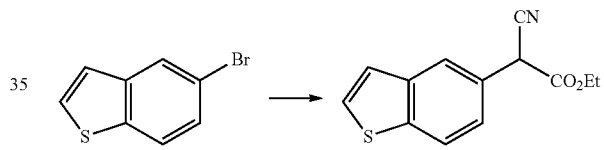

To toluene (3 mL) solution of 0.21 g of ethyl cyanoacetate were added 0.41 g of potassium tert-butoxide, 0.30 g of 5-bromobenzothiophene and 0.02 g of tetrakis(triphenylphosphine)palladium(0), which was then refluxed for 7.5 hours. To the reaction mixture was added water, and the pH was adjusted to 2 with hydrochloric acid. Thereto was added ethyl acetate, and insoluble matter was filtered off. The organic layer was separated, washed with water, and dried over anhydrous magnesium sulfate, followed by distilling off the solvent under reduced pressure. The resultant residue was purified using silica gel column chromatography (eluent; hexane:ethyl acetate=5:1) to provide 0.16 g of ethyl 2-(1-benzothiophen-5-yl)-2-cyanoacetate as pale yellow solid form.

$^1$H-NMR(CDCl$_3$) δ value:
1.29 (3H, t, J=7.1 Hz), 4.25 (2H, m), 4.84 (1H, s), 7.37 (1H, d, J=5.4 Hz), 7.41 (1H, dd, J=8.5, 1.7 Hz), 7.54 (1H, d, J=5.4 Hz), 7.92 (1H, d, J=8.5 Hz), 7.94 (1H, d, J=1.7 Hz).

Example 2-4

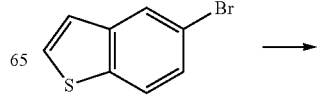

-continued

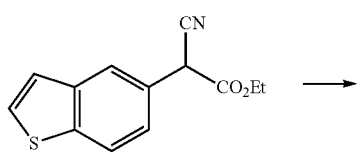

To toluene (25 mL) suspension of 0.16 g of dichlorobis(triphenylphosphine)palladium(II) were added 0.12 g of triphenylphosphine, 0.01 g of sodium borohydride, 5.79 g of potassium tert-butoxide and 2.92 g of ethyl cyanoacetate, which was then stirred at room temperature for 10 minutes. Thereto were added 5.00 g of 5-bromobenzothiophene and 25 mL of toluene, which was then refluxed for 4 hours. Thereto was added 0.14 g of tetrakis(triphenylphosphine)palladium (0), which was then refluxed for 2 hours. Next, to the reaction solution were added 25 mL of ethanol, 2.82 g of sodium hydroxide and 5 mL of water, which was then refluxed for 6 hours. Thereto was added 2.82 g of sodium hydroxide, which was then refluxed for 5 hours. To the reaction mixture were added 15 mL of water and 0.5 g of activated carbon, and insoluble matter was filtered off. The aqueous layer was separated, and to the solution was added 35 mL of ethanol. The pH was adjusted to 2 with 15 mL of hydrochloric acid. Thereto was added 15 mL of water, which was then stirred at 40° C. Thereto was added 30 mL of water, which was stirred. After that, it was cooled. The precipitate was collected by filtration to provide 3.38 g of 2-(1-benzothiophen-5-yl)acetic acid as pale yellow solid form.

The Chemical shift values of $^1$H-NMR spectral in CDCl$_3$ agreed with the values of example 2-1 (2).

Example 2-5

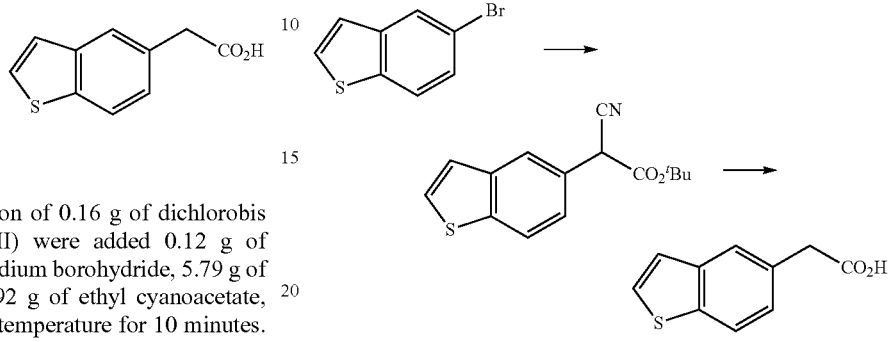

To 1,2-dimethoxyethane (25 mL) suspension of 0.16 g of dichlorobis(triphenylphosphine)palladium(II) were added 0.12 g of triphenylphosphine, 0.01 g of sodium borohydride, 5.53 g of potassium tert-butoxide and 3.48 g of tert-butyl cyanoacetate, which was then stirred at room temperature for 10 minutes. Thereto was added 5.00 g of 5-bromobenzothiophene, which was then refluxed for 2 hours. After to the reaction mixture was added 15 mL of water, the pH was adjusted to 1 with 2 mL of hydrochloric acid. The precipitate was collected by filtration to provide 5.69 g of tert-butyl 2-(1-benzothiophen-5-yl)-2-cyanoacetate as pale yellow solid form.

$^1$H-NMR(CDCl$_3$) δ value:
1.45 (9H, s), 4.73 (1H, s), 7.36 (1H, d, J=5.6 Hz), 7.39 (1H, dd, J=8.5, 2.0 Hz), 7.52 (1H, d, J=5.6 Hz), 7.91 (1H, d, J=8.5 Hz), 7.9-8.0 (1H, m).

Example 2-6

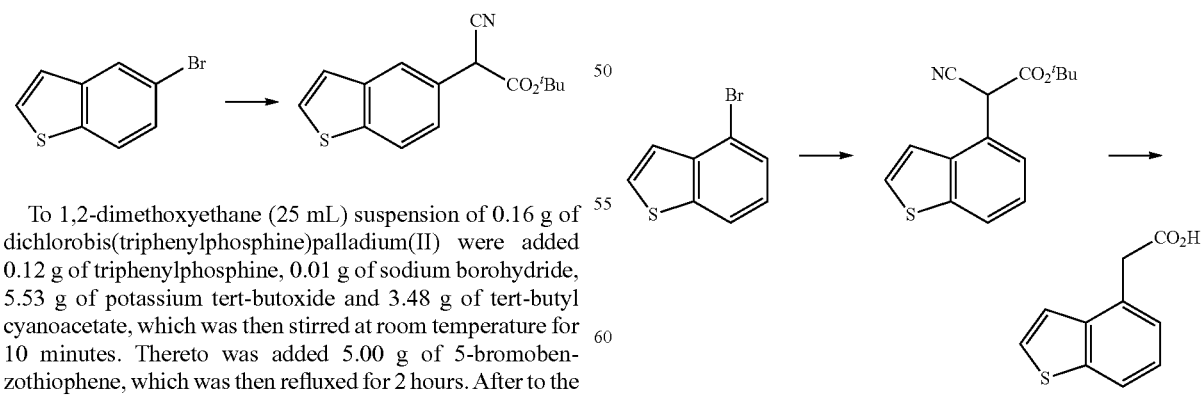

To 1,2-dimethoxyethane (1.00 L) solution of 250 g of 5-bromobenzothiophene were added 276 g of potassium tert-butoxide and 174 g of tert-butyl cyanoacetate. Thereto were added 8.23 g of dichlorobis(triphenylphosphine)palladium (II) and 6.15 g of triphenylphosphine at 80 to 85° C., which was then refluxed for 2 hours. Next, to the reaction mixture were added 500 mL of ethylene glycol, 250 mL of water and 263 g of potassium hydroxide, which was then refluxed for 4 hours. To the reaction mixture were added 1.50 L of water and 12.5 g of kieselguhr (celipure, product of Advanced Minerals Company). After insoluble matter was filtered off, to the filtrate was added 250 mL of toluene, and the aqueous layer was separated. To the aqueous layer were added 375 mL of toluene and 375 mL of ethyl acetate, the pH was adjusted to 1 with 505 mL of hydrochloric acid, and the organic layer was separated. The organic layer was treated with 12.5 g of activated carbon. The solvent was distilled off under reduced pressure, to which was added toluene. The precipitate was collected by filtration to provide 176 g of 2-(1-benzothiophen-5-yl)acetic acid as white solid form.

The Chemical shift values of $^1$H-NMR spectral in CDCl$_3$ agreed with the values of example 2-1 (2).

Example 2-7

To 1,2-dimethoxyethane (3 mL) solution of 0.30 g of 4-bromobenzothiophene were added 0.33 g of potassium tert-butoxide, 0.21 g of tert-butyl cyanoacetate, 0.01 g of dichlorobis(triphenylphosphine)palladium(II) and 0.01 g of triphenylphosphine, which was then refluxed for 40 minutes. Thereto were added 0.33 g of potassium tert-butoxide, 0.01 g of dichlorobis(triphenylphosphine)palladium(II) and 0.01 g of triphenylphosphine, which was then refluxed for 30 minutes. The reaction mixture was added to a mixed solution of water and ethyl acetate, and the pH was adjusted to 1 with 6 mol/L hydrochloric acid. The organic layer was separated, and dried over anhydrous magnesium sulfate, followed by distilling off the solvent under reduced pressure. The resultant residue was purified using silica gel column chromatography (eluent; hexane:ethyl acetate=5:1) to provide 0.26 g of tert-butyl 2-(1-benzothiophen-4-yl)-2-cyanoacetate as pale brown oily form.

$^1$H-NMR(CDCl$_3$) δ value:

1.42 (9H, s), 5.03 (1H, s), 7.39 (1H, t, J=7.8 Hz), 7.49 (1H, d, J=7.8 Hz), 7.54 (1H, d, J=5.6 Hz), 7.59 (1H, d, J=5.6 Hz), 7.92 (1H, d, J=7.8 Hz).

(2) To ethylene glycol (1.0 mL) solution of 0.25 g of tert-butyl 2-(1-benzothiophen-4-yl)-2-cyanoacetate were added 1.0 mL of aqueous solution of 40% (w/w) potassium hydroxide and 0.3 mL of water, which was then stirred at 95 to 105° C. for 1 hour. To the reaction mixture were added water and toluene, and the aqueous layer was separated. The pH was adjusted to 2 with 6 mol/L hydrochloric acid, to which was added ethyl acetate. The organic layer was separated, and dried over anhydrous magnesium sulfate, followed by distilling off the solvent under reduced pressure. To the resultant residue was added cyclohexane. The precipitate was collected by filtration to provide 0.15 g of 2-(1-benzothiophen-4-yl)acetic acid as white solid form.

$^1$H-NMR(CDCl$_3$) δ value:

3.95 (2H, s), 7.2-7.4 (2H, m), 7.41 (1H, d, J=5.5 Hz), 7.47 (1H, d, J=5.5 Hz), 7.82 (1H, d, J=7.8 Hz).

Example 3-1

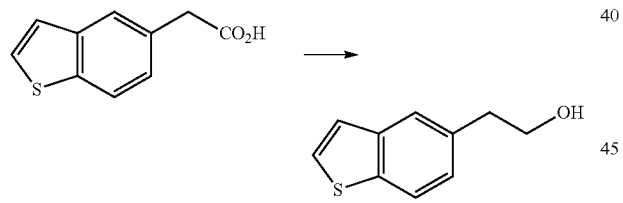

To 340 mL of tetrahydrofuran was suspended 50.2 g of sodium borohydride, to which were dropped tetrahydrofuran (340 mL) solution of 170 g of (1-benzothiophen-5-yl)acetic acid, and 65.1 g of sulfuric acid successively, which was then stirred at room temperature for 2.5 hours. To this reaction mixture was dropwise added 85 mL of acetone, which was then stirred for 30 minutes. Thereto were added 510 mL of water and 680 mL of toluene. The organic layer was separated, to which was added 510 mL of water, and the pH was adjusted to 12 with 48 mL of 20% (w/w) sodium hydroxide aqueous solution. The organic layer was separated, and washed with water, followed by distilling off the solvent. Thereto were added cyclohexane and toluene. The precipitate was collected by filtration to provide 135 g of 2-(1-benzothiophen-5-yl)ethanol as white solid form.

$^1$H-NMR(CDCl$_3$) δ value:

1.41 (1H, t, J=6.0 Hz), 2.99 (2H, t, J=6.5 Hz), 3.8-4.0 (2H, m), 7.22 (1H, dd, J=8.3, 1.7 Hz), 7.30 (1H, d, J=5.4 Hz), 7.44 (1H, d, J=5.4 Hz), 7.6-7.7 (1H, m), 7.83 (1H, d, J=8.3 Hz).

Example 3-2

To 5 mL of 1,2-dimethoxyethane was suspended 2.95 g of sodium borohydride, to which were dropwise added 1,2-dimethoxyethane (25 mL) solution of 10 g of (1-benzothiophen-5-yl)acetic acid, and 11 mL of 6.9 mol/L hydrochloride/1,2-dimethoxyethane solution, which was then stirred at room temperature for 1 hour. To this reaction mixture was dropwise added 5 mL of acetone, which was then stirred for 30 minutes. Thereto were added 20 mL of water, 30 mL of toluene and 2 mL of 2 mol/L hydrochloric acid. Next, after the pH was adjusted to 9.5 with 20 mL of 2 mol/L sodium hydroxide aqueous solution, the organic layer was separated. The organic layer was dried over anhydrous magnesium sulfate, followed by distilling off the solvent. Thereto were added cyclohexane and toluene. The precipitate was collected by filtration to provide 7.84 g of 2-(1-benzothiophen-5-yl)ethanol as white solid form.

Example 3-3

To 40 mL of tetrahydrofuran was suspended 4.72 g of sodium borohydride, to this solution were dropwise added tetrahydrofuran (60 mL) solution of 20 g of (1-benzothiophen-5-yl)acetic acid, and 6.12 g of sulfuric acid. The solution was heated to 66° C., followed by distilling off about 40 mL of the solvent under normal pressure, which was then stirred at same temperature for 1 hour. After cooling, to this reaction mixture was dropwise added 10 mL of acetone, which was then stirred for 30 minutes. Thereto were added 90 mL of water and 80 mL of toluene. The organic layer was separated, to which was added 60 mL of water, and the pH was adjusted to 13.6 with 5 mL of 5 mol/L sodium hydroxide aqueous solution. The organic layer was separated, washed with water, followed by distilling off the solvent, and thereto were added cyclohexane and toluene. The precipitate was collected by filtration to provide 16.5 g of 2-(1-benzothiophen-5-yl)ethanol as white solid form.

The Chemical shift values of $^1$H-NMR spectral in CDCl$_3$ agreed with the values of example 3-1.

Example 4-1

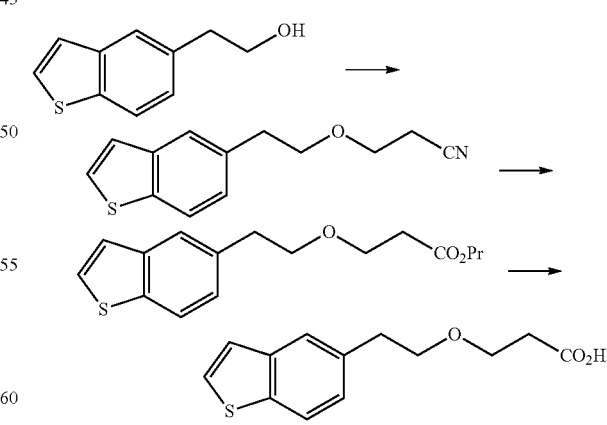

(1) To toluene (5 mL) suspension of 0.23 g of 40% (w/w) benzyltrimethylammonium hydroxide aqueous solution was added 5.00 g of 2-(1-benzothiophen-5-yl)ethanol, and dropwise added 2.20 mL of acrylonitrile at 0 to 5° C., which was then stirred at 0 to 20° C. for 1 hour. To this reaction mixture was added 0.125 mL of hydrochloric acid. Thereto were added 10 mL of propanol, 1.0 mL of water and 3.1 mL of sulfuric acid, which was then refluxed for 6.5 hours. After cooling, to the reaction mixture were added 10 mL of water and 10 mL of toluene. The organic layer was separated, and dried over anhydrous magnesium sulfate. After insoluble matter was filtered off, the solvent was distilled off under reduced pressure. The resultant residue was purified using silica gel column chromatography (eluent; hexane:ethyl acetate=15:1 to 7:1) to provide 7.21 g of propyl 3-(2-(1-benzothiophen-5-yl)ethoxy)propionate as colorless oily form.

$^1$H-NMR(CDCl$_3$) δ value:

0.91 (3H, t, J=7.4 Hz), 1.57-1.67 (2H, m), 2.58 (2H, t, J=6.4 Hz), 2.99 (2H, t, J=7.1 Hz), 3.71 (2H, t, J=7.1 Hz), 3.74 (2H, t, J=6.4 Hz), 4.02 (2H, t, J=6.7 Hz), 7.20 (1H, dd, J=8.2, 1.6 Hz), 7.28 (1H, d, J=5.6 Hz), 7.41 (1H, d, J=5.6 Hz), 7.60-7.70 (1H, m), 7.78 (1H, d, J=8.2 Hz).

(2) To methanol (12 mL) solution of 12.0 g of propyl 3-(2-(1-benzothiophen-5-yl)ethoxy)propionate was added water (12 mL) solution of 2.76 g of potassium hydroxide, which was then stirred at room temperature for 1.5 hours. This reaction mixture was distilled off under reduced pressure, to which were added 36 mL of toluene and 36 mL of water. The pH was adjusted to 1.9 with 8 mL of 6 mol/L hydrochloric acid. The organic layer was separated, followed by distilling off the solvent under reduced pressure. Thereto were added 12 mL of toluene and 24 mL of cyclohexane. The precipitate was collected by filtration to provide 8.91 g of 3-(2-(1-benzothiophen-5-yl)ethoxy)propionic acid as white solid form.

$^1$H-NMR(CDCl$_3$) δ value:

2.63 (2H, t, J=6.2 Hz), 3.00 (2H, t, J=7.1 Hz), 3.72 (2H, t, J=7.1 Hz), 3.74 (2H, t, J=6.2 Hz), 7.20 (1H, dd, J=8.4, 1.6 Hz), 7.27 (1H, dd, J=5.5, 0.6 Hz), 7.40 (1H, d, J=5.5 Hz), 7.65-7.70 (1H, m), 7.78 (1H, d, J=8.4 Hz).

Example 4-2

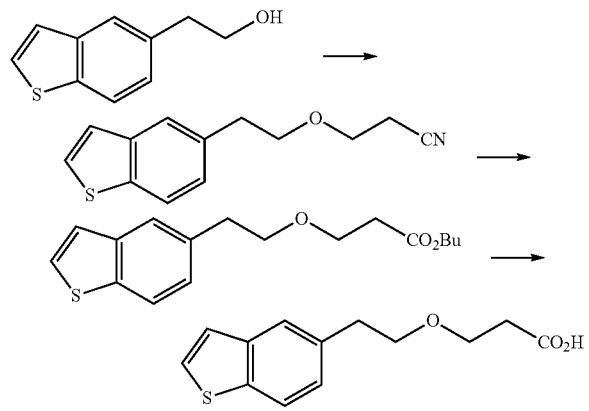

(1) To toluene (5 mL) suspension of 5.00 g of 2-(1-benzothiophen-5-yl)ethanol were added 0.23 g of 40% (w/w) benzyltrimethylammonium hydroxide aqueous solution and 2.28 mL of tetrahydrofuran, and dropwise added 2.20 mL of acrylonitrile at 0 to 10° C., which was then stirred at same temperature for 1.5 hours. To this reaction mixture were added 0.1 mL of hydrochloric acid, 10 mL of butanol and 5 mL of 50% (w/w) sulfuric acid, which was then refluxed for 15 hours. After cooling, to the reaction mixture was added 15 mL of water. The organic layer was separated, and dried over anhydrous magnesium sulfate. After insoluble matter was filtered off, the solvent was distilled off under reduced pressure. The resultant residue was purified using silica gel column chromatography (eluent; hexane:ethyl acetate=10:1) to provide 6.65 g of butyl 3-(2-(1-benzothiophen-5-yl)ethoxy)propionate as colorless oily form.

$^1$H-NMR(CDCl$_3$) δ value:

0.92 (3H, t, J=7.4 Hz), 1.30-1.45 (2H, m), 1.50-1.65 (2H, m), 2.57 (2H, t, J=6.3 Hz), 2.99 (2H, t, J=7.1 Hz), 3.71 (2H, t, J=7.1 Hz), 3.74 (2H, t, J=6.3 Hz), 4.06 (2H, t, J=6.7 Hz), 7.21 (1H, dd, J=8.3, 1.7 Hz), 7.28 (1H, dd, J=5.4, 0.7 Hz), 7.41 (1H, d, J=5.4 Hz), 7.65-7.70 (1H, m), 7.78 (1H, d, J=8.3 Hz).

(2) To methanol (5 mL) solution of 5.00 g of butyl 3-(2-(1-benzothiophen-5-yl)ethoxy)propionate was added water (5 mL) solution of 1.10 g of potassium hydroxide, which was then stirred at room temperature for 2 hours. This reaction mixture was distilled off under reduced pressure, to which were added 30 mL of toluene and 30 mL of water. The pH was adjusted to 1.6 with 3.5 mL of 6 mol/L hydrochloric acid. The organic layer was separated, followed by distilling off the solvent under reduced pressure. Thereto were added 15 mL of toluene and 30 mL of cyclohexane. The precipitate was collected by filtration to provide 3.60 g of 3-(2-(1-benzothiophen-5-yl)ethoxy)propionic acid as white solid form.

The Chemical shift values of $^1$H-NMR spectral in CDCl$_3$ agreed with the values of example 4-1 (2).

Example 4-3

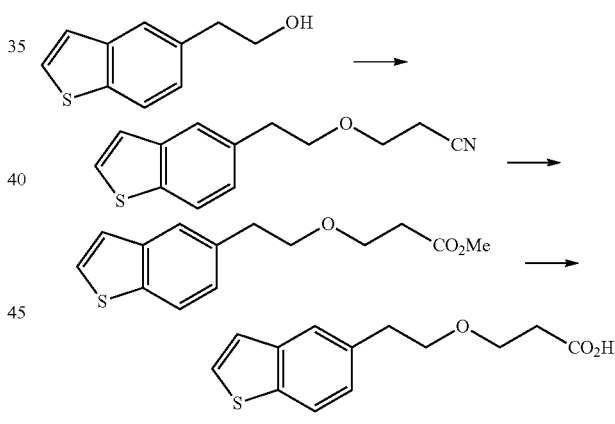

(1) To toluene (5 mL) suspension of 5.00 g of 2-(1-benzothiophen-5-yl)ethanol were added 0.23 g of 40% (w/w) benzyltrimethylammonium hydroxide aqueous solution and 2.28 mL of tetrahydrofuran, and dropwise added 2.22 mL of acrylonitrile at 5° C., which was then stirred at 0 to 15° C. for 1.5 hours. To this reaction mixture were added 0.13 mL of hydrochloric acid, 10 mL of methanol and 1.52 g of water. Thereto was introduced 9.47 g of hydrogen chloride, which was then refluxed for 4 hours. After cooling, to the reaction mixture were added 15 mL of water and 10 mL of toluene. The organic layer was separated, and dried over anhydrous magnesium sulfate. After insoluble matter was filtered off, the solvent was distilled off under reduced pressure. The resultant residue was purified using silica gel column chromatography (eluent; hexane:ethyl acetate=5:1) to provide 7.36 g of methyl 3-(2-(1-benzothiophen-5-yl)ethoxy)propionate as colorless oily form.

$^1$H-NMR(CDCl$_3$) δ value:

2.58 (2H, t, J=6.4 Hz), 2.99 (2H, t, J=7.1 Hz), 3.65 (3H, s), 3.71 (2H, t, J=7.1 Hz), 3.74 (2H, t, J=6.4 Hz), 7.20 (1H, dd, J=8.3, 1.7 Hz), 7.28 (1H, d, J=5.4 Hz), 7.41 (1H, d, J=5.4 Hz), 7.65-7.70 (1H, m), 7.78 (1H, d, J=8.3 Hz).

(2) To methanol (5 mL) solution of 5.00 g of methyl 3-(2-(1-benzothiophen-5-yl)ethoxy)propionate was added water (5 mL) solution of 1.27 g of potassium hydroxide, which was then stirred at room temperature for 2 hours. This reaction mixture was distilled off under reduced pressure, to which were added 30 mL of toluene and 30 mL of water. The pH was adjusted to 1.0 with 5 mL of 6 mol/L hydrochloric acid. The organic layer was separated, followed by distilling off the solvent under reduced pressure. Thereto were added 11 mL of toluene and 30 mL of cyclohexane. The precipitate was collected by filtration to provide 4.51 g of 3-(2-(1-benzothiophen-5-yl)ethoxy)propionic acid as white solid form.

The Chemical shift values of $^1$H-NMR spectral in CDCl$_3$ agreed with the values of example 4-1 (2).

Example 4-4

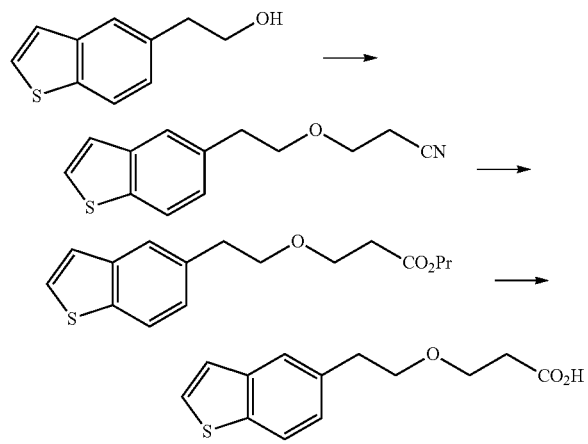

To toluene (50 mL) suspension of 50.0 g of 2-(1-benzothiophen-5-yl)ethanol was added 2.35 g of 40% (w/w) benzyltrimethylammonium hydroxide aqueous solution, and dropwise added 17.9 g of acrylonitrile at 8 to 15° C., which was then stirred at 10 to 20° C. for 1.5 hours. To this reaction mixture were added 1.25 mL of hydrochloric acid, 100 mL of propanol and 5.05 g of water. Thereto was dropwise added 55.0 g of sulfuric acid, which was then refluxed for 6 hours. After cooling, to the reaction mixture was added 100 mL of water. The organic layer was separated. Thereto was added 50 mL of methanol and dropwise added water (50 mL) solution of 31.5 g of potassium hydroxide, which was then stirred at room temperature for 1.5 hours. To this reaction mixture were added 75 mL of toluene and 75 mL of water. The aqueous layer was separated, thereto was added 100 mL of toluene, the pH was adjusted to 0.9 with 6 mol/L hydrochloric acid, and the organic layer was separated. After the solvent was distilled off under reduced pressure, thereto were added 50 mL of toluene and 125 mL of cyclohexane. The precipitate was collected by filtration to provide 59.6 g of 3-(2-(1-benzothiophen-5-yl)ethoxy)propionic acid as white solid form.

The Chemical shift values of $^1$H-NMR spectral in CDCl$_3$ agreed with the values of example 4-1 (2).

Example 4-5

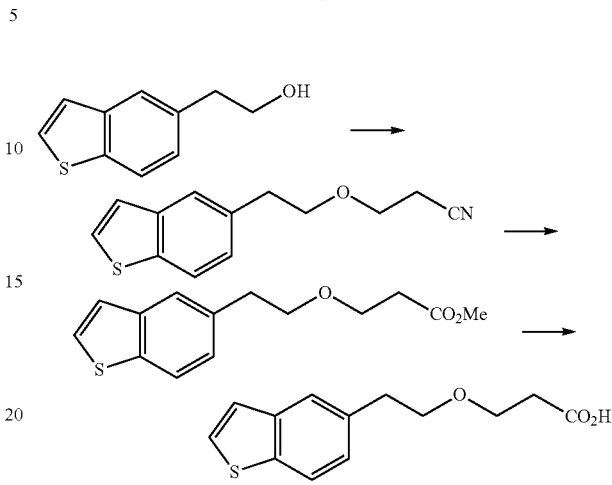

To toluene (260 mL) suspension of 260 g of 2-(1-benzothiophen-5-yl)ethanol were added 43.8 g of 2-propanol and 1.64 g of potassium tert-butoxide, which was then stirred for 0.5 hours. After cooling the reaction mixture to 15° C., thereto was dropwise added 116 g of acrylonitrile, which was then stirred at 15 to 25° C. for 1 hour. To this reaction mixture were added 6.5 mL of hydrochloric acid, 520 mL of methanol and 78.9 g of water. Thereto was introduced 310 g of hydrogen chloride at 10 to 25° C., which was then refluxed for 3 hours. After cooling, to the reaction mixture were added 780 mL of water and 520 mL of toluene, and the organic layer was separated. To the organic layer were dropwise added 260 mL of methanol and water (260 mL) solution of 164 g of potassium hydroxide, which was then stirred at 30 to 35° C. for 2 hours. To this reaction mixture was added 260 mL of water, and the aqueous layer was separated. To the aqueous layer were added 520 mL of toluene and 260 mL of water and dropwise added 234 mL of hydrochloric acid, and the organic layer was separated. After 390 mL of solvent was distilled off under reduced pressure from the organic layer, thereto was added 1040 mL of cyclohexane. The precipitate was collected by filtration to provide 326 g of 3-(2-(1-benzothiophen-5-yl) ethoxy)propionic acid as white solid form.

The Chemical shift values of $^1$H-NMR spectral in CDCl$_3$ agreed with the values of example 4-1 (2).

Example 4-6

To toluene (360 mL) suspension of 180 g of 2-(1-benzothiophen-5-yl)ethanol was added 4.22 g of aqueous solution of 40% (w/w) benzyltrimethylammonium hydroxide, and dropwise added 8.04 g of acrylonitrile at 30° C. After cooling the reaction mixture to 20° C., thereto was dropwise added 53.6 g of acrylonitrile, which was then stirred at 15 to 25° C. for 2 hours. To this reaction mixture were added 27 mL of hydrochloric acid and 180 mL of methanol. Thereto was introduced 97 g of hydrogen chloride at 10 to 25° C., which was then stirred at 30 to 40° C. for 30 minutes and refluxed for 3 hours. After cooling, to the reaction mixture was added 360 mL of water, and the organic layer was separated. To the organic layer were dropwise added 180 mL of methanol, and water (180 mL) solution of 113 g of potassium hydroxide, which was then stirred at 30 to 35° C. for 2 hours. To the reaction mixture was added 360 mL of water, and the aqueous layer was separated. To this aqueous layer was added 360 mL of toluene and dropwise added 151 mL of hydrochloric acid, and the organic layer was separated. After 126 mL of solvent was distilled off under normal pressure from the organic layer, thereto was added 1080 mL of cyclohexane. The precipitate was collected by filtration to provide 222 g of 3-(2-(1-benzothiophen-5-yl)ethoxy)propionic acid as white solid form.

The Chemical shift values of $^1$H-NMR spectral in CDCl$_3$ agreed with the values of example 4-1 (2).

Example 5-1

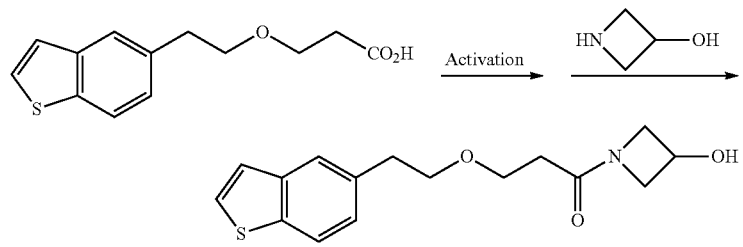

In 15 mL of 1,2-dimethoxyethane was dissolved 10.0 g of 3-(2-(1-benzothiophen-5-yl)ethoxy)propionic acid. Thereto were added 0.1 mL of N,N-dimethylformamide and 5.23 g of thionyl chloride, which was then stirred at room temperature for 1.5 hours. This reaction solution was dropwise added to a mixed solution of 50 mL of water, 7.19 g of sodium hydroxide and 7.69 g of 3-azetidinol 1/2 tartrate at 5 to 15° C., which was then stirred at same temperature for 2 hours. Thereto was added 90 mL of water. The precipitate was collected by filtration to provide 11.0 g of 1-(3-(2-(1-benzothiophen-5-yl)ethoxy)propionyl)azetidin-3-ol as white solid form.

$^1$H-NMR(CDCl$_3$) δ value:

2.25-2.35 (2H, m), 2.96 (2H, t, J=7.0 Hz), 3.65-3.80 (5H, m), 3.85-3.95 (1H, m), 4.05-4.15 (1H, m), 4.15-4.25 (1H, m), 4.40-4.50 (1H, m), 7.19 (1H, dd, J=8.3, 1.5 Hz), 7.27 (1H, d, J=5.4 Hz), 7.40 (1H, d, J=5.4 Hz), 7.62-7.66 (1H, m), 7.78 (1H, d, J=8.3 Hz).

Example 5-2

To 116 mL of toluene was suspended 29.0 g of 3-(2-(1-benzothiophen-5-yl)ethoxy)propionic acid. Thereto were added 0.6 mL of N,N-dimethylformamide and 14.5 g of thionyl chloride, which was then stirred at room temperature for 2 hours. After that, 62 mL of solvent was distilled off under reduced pressure. This reaction solution was dropwise added to a mixed solution of 87 mL of water, 13.9 g of sodium hydroxide and 25.7 g of 3-azetidinol 1/2 tartrate at 10 to 20° C., which was then stirred at 20 to 25° C. for 1 hour and left unattended overnight. After cooling the reaction solution, the pH was adjusted to 6 with 7 mL of acetic acid. After stirring at 10 to 15° C. for 1 hour, the precipitate was collected by filtration to provide 31.9 g of 1-(3-(2-(1-benzothiophen-5-yl)ethoxy)propionyl)azetidin-3-ol as white solid form.

The Chemical shift values of $^1$H-NMR spectral in CDCl$_3$ agreed with the values of example 5-1.

Example 5-3

In 75 mL of 1,2-dimethoxyethane was dissolved 50.0 g of 3-(2-(1-benzothiophen-5-yl)ethoxy)propionic acid. Thereto was added 26.1 g of thionyl chloride, which was then refluxed for 2 hours. After cooling, this reaction solution was dropwise added to a mixed solution of 125 mL of water, 20.0 g of sodium hydroxide and 25.2 g of 3-azetidinol hydrochloride at −5 to 10° C., which was then stirred at 0 to 15° C. for 30 minutes. Thereto was added 75 mL of water, which was heated to 40° C. and dissolved. After cooling, the precipitate was collected by filtration to provide 56.5 g of 1-(3-(2-(1-benzothiophen-5-yl)ethoxy)propionyl)azetidin-3-ol as white solid form.

The Chemical shift values of $^1$H-NMR spectral in CDCl$_3$ agreed with the values of example 5-1.

Example 6-1

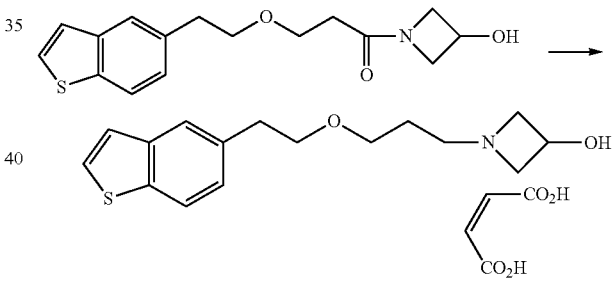

To bis(2-methoxyethyl)ether (5 mL) suspension of 1.00 g of 1-(3-(2-(1-benzothiophen-5-yl)ethoxy)propionyl)azetidin-3-ol was added 0.37 g of sodium borohydride, which was then cooled to 10° C. Thereto was dropwise added 2.49 mL of chlorotrimethylsilane at 5 to 10° C. for 20 minutes, which was then stirred at room temperature for 2.5 h and at 40° C. for 4 hours. After cooling, thereto was dropwise added 3.27 mL of 6.0 mol/L hydrochloric acid, which was then stirred at 70 to 75° C. for 30 minutes. To the reaction mixture were added water and ethyl acetate, and the pH was adjusted to 10.0 with 2.0 mol/L sodium hydroxide aqueous solution. The organic layer was separated, washed sequentially with water and saturated sodium chloride aqueous solution. Thereto were added anhydrous magnesium sulfate and activated carbon. After insoluble matter was filtered off, the solvent was distilled off under reduced pressure. To the resultant residue was added 0.36 g of maleic acid, which was solidified from a mixed solvent (5 mL) of ethyl acetate:2-propanol (4:1) to provide 0.72 g of 1-(3-(2-(1-benzothiophen-5-yl)ethoxy)propyl)azetidin-3-ol maleate as colorless crystal form.

$^1$H-NMR (DMSO-d$_6$) δ value:
1.65-1.75 (2H, m), 2.93 (2H, t, J=6.9 Hz), 3.14 (2H, t, J=7.4 Hz), 3.44 (2H, t, J=6.0 Hz), 3.63 (2H, t, J=6.9 Hz), 3.75-3.85 (2H, m), 4.15-4.25 (2H, m), 4.40-4.50 (1H, m), 6.06 (2H, s), 7.26 (1H, dd, J=8.3, 1.5 Hz), 7.41 (1H, d, J=5.4 Hz), 7.73 (1H, d, J=5.4 Hz), 7.70-7.75 (1H, m), 7.91 (1H, d, J=8.3 Hz).

Example 6-2

To 1,2-dimethoxyethane (5 mL) suspension of 1.00 g of 1-(3-(2-(1-benzothiophen-5-yl)ethoxy)propionyl)azetidin-3-ol was added 0.37 g of sodium borohydride, which was then cooled to 10° C. Thereto was dropwise added 2.49 mL of chlorotrimethylsilane at 5 to 10° C., which was then stirred at room temperature for 2.5 h and at 40° C. for 4 hours. After cooling, thereto was dropwise added 3.27 mL of 6.0 mol/L hydrochloric acid, which was then stirred at 70 to 75° C. for 30 minutes. To the reaction mixture were added water and ethyl acetate, and the pH was adjusted to 10.0 with 2.0 mol/L sodium hydroxide aqueous solution. The organic layer was separated, washed sequentially with water and saturated sodium chloride aqueous solution. Thereto were added anhydrous magnesium sulfate and activated carbon. After insoluble matter was filtered off, the solvent was distilled off under reduced pressure. To the resultant residue was added 0.36 g of maleic acid, which was solidified from a mixed solvent (5 mL) of ethyl acetate:2-propanol (4:1) to provide 0.71 g of 1-(3-(2-(1-benzothiophen-5-yl)ethoxy)propyl)azetidin-3-ol maleate as colorless crystal form.

The Chemical shift values of $^1$H-NMR spectral in DMSO-d$_6$ agreed with the values of example 6-1.

Example 6-3

To tetrahydrofuran (5 mL) suspension of 1.00 g of 1-(3-(2-(1-benzothiophen-5-yl)ethoxy)propionyl)azetidin-3-ol was added 0.37 g of sodium borohydride, and dropwise added tetrahydrofuran (1 mL) solution of 0.75 mL of trifluoroacetic acid for 30 minutes, which was then refluxed for 2 hours. After cooling, thereto was dropwise added 3.27 mL of 6.0 mol/L hydrochloric acid, which was then refluxed for 1.5 hours. To the reaction mixture were added water and ethyl acetate, and the aqueous layer was separated. To the aqueous layer was added ethyl acetate, and the pH was adjusted to 10.0 with 20% (w/w) sodium hydroxide aqueous solution. The organic layer was separated, washed sequentially with water and saturated sodium chloride aqueous solution, and dried over anhydrous magnesium sulfate. After insoluble matter was filtered off, the solvent was distilled off under reduced pressure. To the resultant residue was added 0.36 g of maleic acid, which was solidified from a mixed solvent (5 mL) of ethyl acetate:2-propanol (4:1) to provide 0.62 g of 1-(3-(2-(1-benzothiophen-5-yl)ethoxy)propyl)azetidin-3-ol maleate as colorless crystal form.

The Chemical shift values of $^1$H-NMR spectral in DMSO-d$_6$ agreed with the values of example 6-1.

Example 6-4

To tetrahydrofuran (3 mL) suspension of 0.50 g of 1-(3-(2-(1-benzothiophen-5-yl)ethoxy)propionyl)azetidin-3-ol was added 0.19 g of sodium borohydride, which was then heated to 50° C. Thereto was dropwise added tetrahydrofuran (1 mL) solution of 0.46 mL of dimethyl sulfate at 50 to 55° C. for 10 minutes, which was then stirred at same temperature for 2.5 hours. After cooling, thereto was dropwise added 1.64 mL of 6.0 mol/L hydrochloric acid, which was then refluxed for 1.5 hours. To the reaction mixture was added ethyl acetate, and the pH was adjusted to 10.0 with 20% (w/w) sodium hydroxide aqueous solution. The organic layer was separated, washed sequentially with water and saturated sodium chloride aqueous solution, and dried over anhydrous magnesium sulfate. After insoluble matter was filtered off, the solvent was distilled off under reduced pressure. To the resultant residue was added 0.18 g of maleic acid, which was solidified from a mixed solvent (3.75 mL) of ethyl acetate:2-propanol (4:1) to provide 0.49 g of 1-(3-(2-(1-benzothiophen-5-yl)ethoxy)propyl)azetidin-3-ol maleate as colorless crystal form.

The Chemical shift values of $^1$H-NMR spectral in DMSO-d$_6$ agreed with the values of example 6-1.

Example 6-5

To bis(2-methoxyethyl)ether (5 mL) suspension of 1.00 g of 1-(3-(2-(1-benzothiophen-5-yl)ethoxy)propionyl)azetidin-3-ol was added 0.37 g of sodium borohydride, which was then cooled to 10° C. Thereto was dropwise added 2.46 mL of 4.0 mol/L hydrogen chloride/dioxane at 5 to 15° C. for 12 minutes, which was then stirred at same temperature for 30 minutes, at room temperature for 3 hours and at 35 to 40° C. for 6 hours. After cooling, thereto was dropwise added 3.27 mL of 6.0 mol/L hydrochloric acid, which was then stirred at 65 to 70° C. for 1.5 hours. To the reaction mixture were added water and ethyl acetate, and the pH was adjusted to 10.0 with 2.0 mol/L sodium hydroxide aqueous solution. The organic layer was separated, washed sequentially with water and saturated sodium chloride aqueous solution. Thereto were added anhydrous magnesium sulfate and activated carbon. After insoluble matter was filtered off, the solvent was distilled off under reduced pressure. To the resultant residue was added 0.36 g of maleic acid, which was solidified from a mixed solvent (5 mL) of ethyl acetate:2-propanol (4:1) to provide 0.86 g of 1-(3-(2-(1-benzothiophen-5-yl)ethoxy)propyl)azetidin-3-ol maleate as colorless crystal form.

$^1$H-NMR in DMSO-d$_6$ agreed with the values of example 6-1.

Example 6-6

To 1,2-dimethoxyethane (5 mL) suspension of 1.00 g of 1-(3-(2-(1-benzothiophen-5-yl)ethoxy)propionyl)azetidin-3-ol was added 0.37 g of sodium borohydride, which was then cooled to 10° C. Thereto was dropwise added 2.46 mL of 4.0 mol/L hydrogen chloride/dioxane at 5 to 15° C. for 10 minutes, which was then stirred at same temperature for 1 hour, at room temperature for 3.5 hours and at 35 to 40° C. for 6 hours. After cooling, thereto was dropwise added 3.27 mL of 6.0 mol/L hydrochloric acid, which was then stirred at 65 to 70° C. for 1.5 hours. To the reaction mixture were added water and ethyl acetate, and the pH was adjusted to 10.0 with 2.0 mol/L sodium hydroxide aqueous solution. The organic layer was separated, washed sequentially with water and saturated sodium chloride aqueous solution. Thereto were added anhydrous magnesium sulfate and activated carbon. After insoluble matter was filtered off, the solvent was distilled off under reduced pressure. To the resultant residue was added 0.36 g of maleic acid, which was solidified from a mixed solvent (5 mL) of ethyl acetate:2-propanol (4:1) to provide 0.93 g of 1-(3-(2-(1-benzothiophen-5-yl)ethoxy)propyl)azetidin-3-ol maleate as colorless crystal form.

$^1$H-NMR in DMSO-d$_6$ agreed with the values of example 6-1.

Example 6-7

To 1,2-dimethoxyethane (70 mL) suspension of 20.0 g of 1-(3-(2-(1-benzothiophen-5-yl)ethoxy)propionyl)azetidin- 3-ol was added 5.46 g of sodium borohydride, which was then cooled to 15° C. Thereto was dropwise added 20.6 mL of 7.0 mol/L hydrogen chloride/1,2-dimethoxyethane at 15 to 20° C. for 40 minutes, which was then stirred at room temperature for 1.5 hours and at 53 to 57° C. for 4 hours. After cooling, thereto was dropwise added 65.5 mL of 6.0 mol/L hydrochloric acid, which was then stirred at 65 to 70° C. for 1 hour. The reaction mixture was concentrated under reduced pressure, thereto were added 100 mL of water and 100 mL of ethyl acetate, and the pH was adjusted to 10.0 with 5.0 mol/L sodium hydroxide aqueous solution. After the organic layer was separated, washed with 50 mL of water, and the pH was adjusted to 1.0 with 6.0 mol/L hydrochloric acid. The aqueous layer was separated, to which was added 50 mL of ethyl acetate. The pH was adjusted to 10.0 with 5.0 mol/L sodium hydroxide aqueous solution. The organic layer was separated, to which was added anhydrous magnesium sulfate. After insoluble matter was filtered off, the solvent was distilled off under reduced pressure. To the resultant residue was added 7.22 g of maleic acid, which was solidified from a mixed solvent (100 mL) of ethyl acetate:2-propanol (4:1) to provide 19.2 g of 1-(3-(2-(1-benzothiophen-5-yl)ethoxy)propyl)azetidin-3-ol maleate as colorless crystal form.

Example 6-8

To tetrahydrofuran (35.0 mL) suspension of 5.00 g of 1-(3-(2-(1-benzothiophen-5-yl)ethoxy)propionyl)azetidin-3-ol was added 1.61 g of sodium borohydride, and dropwise added tetrahydrofuran (15 mL) solution of 2.09 g of sulfuric acid at room temperature for 30 minutes, which was then stirred at 48 to 52° C. for 7.5 hours. After cooling, thereto was dropwise added 16.4 mL of 6.0 mol/L hydrochloric acid, which was then refluxed for 1 hour. The reaction mixture was concentrated under reduced pressure, thereto were added water and ethyl acetate, and the pH was adjusted to 9.5 with 5.0 mol/L sodium hydroxide aqueous solution. The organic layer was separated, and washed with saturated sodium chloride aqueous solution. Thereto were added anhydrous magnesium sulfate and activated carbon. After insoluble matter was filtered off, the solvent was distilled off under reduced pressure. To the resultant residue was added 1.81 g of maleic acid, which was solidified from a mixed solvent (25 mL) of ethyl acetate:2-propanol (4:1) to provide 4.82 g of 1-(3-(2-(1-benzothiophen-5-yl)ethoxy)propyl)azetidin-3-ol maleate as colorless crystal form.

$^1$H-NMR in DMSO-$d_6$ agreed with the values of example 6-1.

Example 6-9

To tetrahydrofuran (2.38 L) suspension of 340 g of 1-(3-(2-(1-benzothiophen-5-yl)ethoxy)propionyl)azetidin-3-ol was added 110 g of sodium borohydride, and dropwise added tetrahydrofuran (1.02 L) solution of 142 g of sulfuric acid at room temperature for 1 hour, which was then stirred at 45 to 55° C. for 5 hours. After cooling, thereto was added 170 mL of acetone and dropwise added 204 mL of 36% hydrochloric acid, which was then stirred at room temperature for 3 hours and left unattended overnight. To the reaction mixture was added 1.02 L of water, and 3.34 L of the solvent was distilled off under reduced pressure. After cooling, thereto was added 0.68 L of ethyl acetate, and dropwise added water (0.68 L) solution of 147 g of sodium hydroxide at 14 to 22° C., which was then stirred at 7 to 15° C. for 30 minutes. Insoluble matter was filtered off, washed with 0.34 L of ethyl acetate. The filtrate and washings were combined, and the organic layer was separated, washed with 0.68 L of water. After to the organic layer was added 2.04 L of 2-propanol, 3.01 L of the solvent was distilled off under reduced pressure. Thereto were added 1.02 L of ethyl acetate and 34 g of activated carbon, which was stirred for 20 minutes. Insoluble matter was filtered off and washed with 0.34 L of ethyl acetate. The filtrate and washings were combined, thereto was added 116 g of maleic acid. After this reaction mixture was heated and dissolved, it was slowly cooled. The precipitate was collected by filtration to provide 376 g of 1-(3-(2-(1-benzothiophen-5-yl)ethoxy)propyl)azetidin-3-ol maleate as colorless crystal form.

$^1$H-NMR in DMSO-$d_6$ agreed with the values of example 6-1.

Example 6-10

To tetrahydrofuran (250 mL) suspension of 50.0 g of 1-(3-(2-(1-benzothiophen-5-yl)ethoxy)propionyl)azetidin-3-ol was added 13.6 g of sodium borohydride, and dropwise added 18.5 g of sulfuric acid at room temperature for 3 hours, which was then stirred at 45 to 55° C. for 4.5 hours. After cooling, thereto was added 15 mL of acetone and dropwise added 120 mL of 6.0 mol/L hydrochloric acid, which was then refluxed for 1 hour. To the reaction mixture was added 150 mL of water, and the solvent was distilled off under reduced pressure. Thereto was added 200 mL of ethyl acetate, and dropwise added water (100 mL) solution of 43.9 g of sodium hydroxide at 10 to 21° C. The organic layer was separated, washed with 20% sodium chloride aqueous solution. Thereto were added 50.0 g of zeolite and 5.0 g of activated carbon, which was then stirred for 20 minutes. Insoluble matter was filtered off and washed with 100 mL of ethyl acetate. The filtrate and washings were combined, thereto were added 63 mL of ethyl acetate, 75 mL of 2-propanol and 17.1 g of maleic acid. After this reaction mixture was heated and dissolved, it was slowly cooled. The precipitate was collected by filtration to provide 56.7 g of 1-(3-(2-(1-benzothiophen-5-yl)ethoxy)propyl)azetidin-3-ol maleate as colorless crystal form.

$^1$H-NMR in DMSO-$d_6$ agreed with the values of example 6-1.

INDUSTRIAL APPLICABILITY

The process for production of 1-(3-(2-(1-benzothiophen-5-yl)ethoxy)propyl)azetidin-3-ol and salts thereof of the present invention has the following characteristics, (1) safety to human body, (2) low environmental loads and (3) a possibility of mass production, and so forth, therefore, the process of 1-(3-(2-(1-benzothiophen-5-yl)ethoxy)propyl)azetidin-3-ol and salts thereof is useful as industrial manufacturing process.

The invention claimed is:

1. A process for production of 1-(3-(2-(1-benzothiophen-5-yl)ethoxy)propyl)azetidin-3-ol, a salt of 1-(3-(2-(1-benzothiophen-5-yl)ethoxy)propyl)azetidin-3-ol, or a combination thereof, the process comprising:
   (A) reducing 1-(3-(2-(1-benzothiophen-5-yl)ethoxy)propionyl)azetidin-3-ol with an activator in the presence of an alkali metal borohydride,
   wherein the activator is at least one compound selected from the group consisting of a protonic acid, a methylating agent, and a silylating agent.

2. The process of claim 1, wherein the activator is sulfuric acid.

3. The process of claim 1, wherein the alkali metal borohydride is sodium borohydride.

4. The process of claim 2, wherein an amount of the sulfuric acid employed is 0.5 to 0.6 times mole per mole of the alkali metal borohydride, and the process comprises adding sulfuric acid at 0 to 30° C. for from 10 minutes to 6 hours, and subsequently reducing at from 30 to 70° C.

5. The process of claim 1, wherein the activator is a protonic acid.

6. The process of claim 1, wherein the activator is a methylating agent.

7. The process of claim 1, wherein the activator is a silylating agent.

8. The process of claim 1, carried out in a solvent.

9. The process of claim 5, wherein the activator is at least one protonic acid selected from the group consisting of HCl and $H_2SO_4$.

10. The process of claim 9, wherein the activator is HCl.

11. The process of claim 5, wherein the alkali metal borohydride is sodium borohydride.

12. The process of claim 1, wherein the reducing is in the absence of a boron trifluoride complex.

13. The process of claim 12, wherein the activator is a protonic acid.

14. The process of claim 12, wherein the alkali metal borohydride is sodium borohydride.

* * * * *